US011203641B2

(12) United States Patent
Mehlen et al.

(10) Patent No.: US 11,203,641 B2
(45) Date of Patent: Dec. 21, 2021

(54) SCREENING FOR ANTI-CANCER COMPOUNDS USING NETRIN-1 ACTIVITY

(71) Applicants: Centre National de la Recherche Scientifique (CNRS), Paris (FR); Centre Leon Berard, Lyons (FR)

(72) Inventors: Patrick Mehlen, Serezin du Rhone (FR); Agnes Bernet, Genas (FR); Julien Fitamant, Lyons (FR)

(73) Assignees: CENTRE NATIONAL DE LA RECHERCHE SCIENTIFIQUE (CNRS), Paris (FR); CENTRE LEON BERARD, Lyons (FR)

(*) Notice: Subject to any disclaimer, the term of this patent is extended or adjusted under 35 U.S.C. 154(b) by 298 days.

(21) Appl. No.: 16/014,529

(22) Filed: Jun. 21, 2018

(65) Prior Publication Data

US 2018/0291106 A1 Oct. 11, 2018

Related U.S. Application Data

(63) Continuation of application No. 14/486,124, filed on Sep. 15, 2014, now abandoned, which is a continuation of application No. 12/224,384, filed as application No. PCT/EP2007/051920 on Feb. 28, 2007, now abandoned.

(60) Provisional application No. 60/776,926, filed on Feb. 28, 2006.

(51) Int. Cl.
| | |
|---|---|
| G01N 33/574 | (2006.01) |
| A61K 39/00 | (2006.01) |
| C07K 16/28 | (2006.01) |
| C12Q 1/18 | (2006.01) |
| C07K 16/22 | (2006.01) |

(52) U.S. Cl.
CPC .......... *C07K 16/2863* (2013.01); *C07K 16/22* (2013.01); *C12Q 1/18* (2013.01); *G01N 33/574* (2013.01); *C07K 2317/732* (2013.01); *C07K 2317/76* (2013.01); *G01N 2333/475* (2013.01); *G01N 2500/02* (2013.01); *G01N 2800/52* (2013.01)

(58) Field of Classification Search
CPC ................ C07K 16/2863; C07K 16/22; C07K 2317/76; C12Q 1/18; G01N 33/574
See application file for complete search history.

(56) References Cited

U.S. PATENT DOCUMENTS

| | | | |
|---|---|---|---|
| 5,565,331 | A | 10/1996 | Tessier-Lavigne et al. |
| 5,824,775 | A | 10/1998 | Swimmer et al. |
| 6,017,714 | A | 1/2000 | Tessier-Lavigne et al. |
| 6,028,173 | A | 2/2000 | Landes et al. |
| 6,030,806 | A | 2/2000 | Landes et al. |
| 6,096,866 | A | 8/2000 | Tessier-Lavigne et al. |
| 6,218,526 | B1 | 4/2001 | Swimmer et al. |
| 6,309,638 | B1 | 10/2001 | Tessier-Lavigne et al. |
| 6,670,451 | B2 | 12/2003 | Tessier-Lavigne et al. |
| 7,041,806 | B2 | 5/2006 | Tessier-Lavigne et al. |
| 7,456,151 | B2 | 11/2008 | Li et al. |
| 7,999,972 | B2 | 8/2011 | Goto et al. |
| 8,097,253 | B2 | 1/2012 | Li et al. |
| 8,168,593 | B2 | 5/2012 | Plouet et al. |
| 2006/0019896 | A1* | 1/2006 | Li .................. A61K 38/179 |
| | | | 514/8.1 |
| 2006/0153840 | A1* | 7/2006 | Eichmann ......... C12N 15/8509 |
| | | | 424/143.1 |

FOREIGN PATENT DOCUMENTS

| | | |
|---|---|---|
| CA | 2489780 A1 | 7/2006 |
| WO | 2005074556 A2 | 8/2005 |
| WO | 2006019904 A1 | 2/2006 |
| WO | 2006054000 A2 | 5/2006 |
| WO | 2009141440 A1 | 11/2009 |

OTHER PUBLICATIONS

Mazelin et al (Nature 431:80-84, Sep. 2004 (Year: 2004).*
Ackerman, S.L., et al., "The mouse rostral cerebellar malformation gene encodes an UNC-5-like protein", Nature, vol. 386, pp. 838-842 (1997).
Andre, F. et al., "Breast Cancer with Synchronous Metastases: Trends in Survival During a 14-Year Period", J. Clin. Oncol., vol. 22, pp. 3302-3308 (2004).
Arakawa et al., "Netrin-I and its Receptors in Tumorigenesis," Nature, Dec. 2004, vol. 4, pp. 978-987.
Arakawa et al., "Netrin-1 and its Receptors in Tumorigenesis," Nature, vol. 4, pp. 978-987, Dec. 2004.
Aslakson, C.J. et al., "Selective Events in the Metastatic Process Defined by Analysis of the Sequential Dissemination of Subpopulations of a Mouse Mammary Tumor", Cancer Research, vol. 52, pp. 1399-1405 (1992).
Bernet, A. et al., "Inactivation of the UNC5C Netrin-1 Receptor is Associated with Tumor Progression in Colorectal Malignancies", Gastroenterology, vol. 133, pp. 1840-1848 (2007).

(Continued)

*Primary Examiner* — Lei Yao
(74) *Attorney, Agent, or Firm* — Rouget F. Henschel; Potomac Law Group, PLLC

(57) ABSTRACT

The subject matter of the present invention relates to an in vitro method for the screening of anti-cancer compounds based on the capacity for these compound to interact with netrin-1 receptor and/or to inhibit the dimerization of the intracellular domain of the netrin-1 receptor expressed in tumor cells. The invention also relates to a method for predicting the presence of metastatic or aggressive cancer, or for determining the efficiency of an anti-cancer treatment based on the measuring of the expression level of netrin-1. The invention further comprises kits and compounds as a medicament for the treatment of cancer such as metastatic breast cancer, related to the overexpression of netrin-1 by the tumor cells.

13 Claims, 17 Drawing Sheets

Figure 1A:
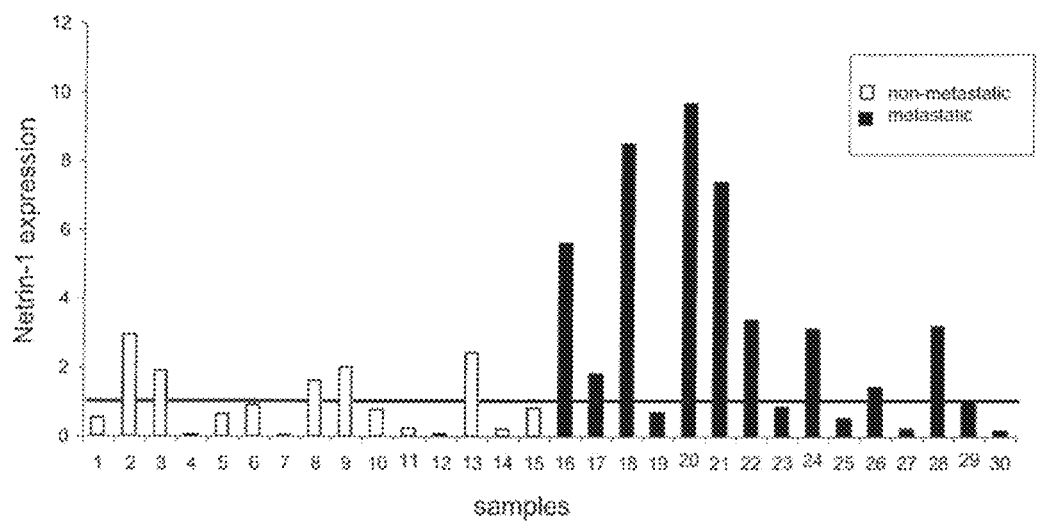

Specification includes a Sequence Listing.

(56) References Cited

OTHER PUBLICATIONS

Bernet, A. et al., "Netrin-1 and its dependence receptors: role in colorectal cancers", Pathologie Biologie, vol. 53, pp. 328-333 (2005).

Bordeaux, M.C. et al., "The RET proto-oncogene induces apoptosis: a novel mechanism for Hirschsprung disease", The EMBO Journal, vol. 19, pp. 4045-4063 (2000).

Braisted et al., "Netrin-1 Promotes Thalamic Axon Growth and is Required for Proper Development of the Thalmocortical Projection," The Journal of Neuroscience, vol. 20, No. 15, pp. 5792-5801, Aug. 1, 2000.

Bredesen, D.E. et al., "Receptors that mediate cellular dependence", Cell Death Differentiation, vol. 12, pp. 1031-1043 (2005).

Bredeson et al., "Apoptosis and Dependence Receptors: A Molecular Basis for Cellular Addiction," Physiol. Rev., vol. 84, pp. 411-430, 2004.

Brunet et al., "Netrin-1 controls sympathetic arterial innervation," The Journal of Clinical Investigation, vol. 124, No. 7, pp. 3230-3240, Jul. 2014.

Chan, S.S. et al., "UNC-40, a C. elegans Homolog of DCC (Deleted in Colorectal Cancer), is Required in Motile Cells Responding to UNC-6 Netrin Cues", Cell, vol. 87, pp. 187-195 (1996).

De Cremoux, P. et al., "Inter-laboratory quality control for hormone-dependent gene expression in human breast tumors using real-time reverse transcription-polymerase chain reaction", Endocrine-Related Cancer, vol. 11, pp. 489-495 (2004).

De Kok, J. et al., "Normalization of gene expression measurements in tumor tissues: comparison of 13 endogenous control genes", Lab Invest., vol. 85, pp. 154-159 (2005).

Ellerby, L.M. et al., "Kennedy's Disease: Caspase Cleavage of the Androgen Receptor is a Crucial Event in Cytotoxicity", Journal of Neurochemistry, vol. 72, pp. 185-195 (1999).

Fazeli, A. et al., "Phenotype of mice lacking functional Deleted in colorectal cancer (DCC) gene", Nature, vol. 386, pp. 796-804 (1997).

Fearon et al., "Cell Survival Guide," Nature, vol. 431, pp. 35-36, Sep. 2004.

Fearon, E.R. et al., "Identification of a Chromosome 18q Gene that is Altered in Colorectal Cancers", Science, vol. 247, pp. 49-56 (1990).

Fitament et al., "Netrin-1 expression confers a selective advantage for tumor cell survival in metastatic breast cancer," PNAS, vol. 105, No. 12, pp. 4850-4855, Mar. 25, 2008.

Forcet, C. et al., "Netrin-1-mediated axon outgrowth requires deleted in colorectal cancer-dependent MAPK activation", Nature, vol. 417, pp. 443-447 (2002).

Forcet, C. et al., "The dependence receptor DCC (deleted in colorectal cancer) defines an alternative mechanism for caspase activation", Proc. Natl. Acad. Sci., vol. 98, pp. 3416-3421 (2001).

Geisbrecht, B.V. et al., "Netrin Binds Discrete Subdomains of DCC and UNC5 and Mediates Interactions between DCC and Heparin", J. Biol. Chem., vol. 278, pp. 32561-32568 (2003).

Hedgecock, E.M. et al., "The unc-5, unc-6, and unc-40 Genes Guide Circumferential Migrations of Pioneer Axons and Mesodermal Cells on the Epidermis in C. elegans", Neuron, vol. 2, pp. 61-85 (1990).

Hong, K. et al., "A Ligand-Gated Association between Cytoplasmic Domains of UNC5 and DCC Family Receptors Converts Netrin-Induced Growth Cone Attraction to Repulsion", Cell, vol. 97, pp. 927-941 (1999).

Inbal, B. et al., "DAP kinase links the control of apoptosis to metastasis", Nature, vol. 390, pp. 180-184 (1997).

Keino-Masu, K. et al., "Deleted in Colorectal Cancer (DCC) Encodes a Netrin Receptor", Cell, vol. 87, pp. 175-185 (1996).

Kinzler, K. et al., "Lessons from Hereditary Colorectal Cancer", Cell, vol. 87, pp. 159-170 (1996).

Kruger, R.P. et al., "Mapping Netrin Receptor Binding Reveals Domains of Unc5 Regulating its Tyrosine Phosphorylation", J. Neurosci., vol. 24, pp. 10826-10834 (2004).

Latil, A. et al., "Quantification of Expression of Netrins, Slits and their Receptors in Human Prostate Tumors", Int. J. Cancer, vol. 103, pp. 306-315 (2003).

Leonardo, E.D. et al. "Vertebrate homologues of C. elegans UNC-5 are candidate netrin receptors". Nature, vol. 386, Apr. 24, 1997, pp. 833-838.

Li et al., "Rac1 and Cdc42 but Not RhoA or Rho Kinase Activities Are Required for Neurite Outgrowth induced by the Netrin-1 Receptor DCC (Deleted In Colorectal Cancer) in N1E-115 Neuroblastoma Cells," The Journal of Biological Chemistry, vol. 277, No. 17, p. 15207-15214, 2002.

Liu, Y. et al., "Novel Role for Netrins in Regulating Epithelial Behavior during Lung Branching Morphogensis", Curr. Biol., vol. 14, pp. 897-905 (2004).

Llambi, F. et al., "Netrin-1 acts as a survival factor via its receptors UNC5H and DCC", The EMBO Journal, vol. 20, pp. 2715-2722 (2001).

Llambi, F. et al., "The dependence receptor UNC5H2 mediates apoptosis through DAP-kinase", The EMBO Journal, pp. 1-10 (2005).

Lu, X. et al., "The netrin receptor UNC5B mediates guidance events controlling morphogensis of the vascular system", Nature, vol. 432, pp. 179-186 (2004).

Matsunaga, E. et al., "RGM and its receptor neogenin regulate neuronal survival", Nat. Cell Biol., vol. 6, pp. 749-755 (2004).

Mazelin et al., "Netrin-I controls colorectal tumorigenesis by regulating apoptosis," Nature, 2004, vol. 431, pp. 80-84.

Mazelin, L. et al., "Netrin-1 controls colorectal tumorigensis by regulating apoptosis", Nature, vol. 431, pp. 80-84 (2004).

Mehlen, P. et al. "The DCC gene product induces apoptosis by a mechanism requiring receptor proteolysis". Nature, vol. 395, Oct. 22, 1998, pp. 801-804.

Mehlen, P. et al., "Dependence receptors: between life and death", Cell Mol. Life Sci., vol. 61, pp. 1854-1866 (2004).

Mehlen, P. et al., "Netrin-1: when a neuronal guidance cue turns out to be a regulator of tumorigensis", Cell Mol. Life Sci., pp. 1-18 (2005).

Mehlen, P. et al., "Role of the Dependence Receptor DCC in Colorectal Cancer Pathogenesis", J. Clin. Oncol., vol. 22, pp. 3420-3428 (2004).

Mehlen, P. et al., "The DCC gene product induces apoptosis by a mechanism requiring receptor proteolysis", Nature, vol. 395, pp. 801-804 (1998).

Mehlen, P. et al., "The dependence receptor hypothesis", Apoptosis, vol. 9, pp. 37-49 (2004).

Mille et al., "Interfering with multimerization of netrin-1 cell receptors triggers tumor cell death," Cell Death Differ., vol. 16, No. 10, 1344-1351. Oct. 2009.

Muppidi, J.R. et al., "Life and Death Decisions: Secondary Complexes and Lipid Rafts in TNF Receptor Family Signal Transduction", Immunity, vol. 21, pp. 461-465 (2004).

Nguyen, A. et al., "Netrin-1 induces angiogensis via a DCC-dependent ERK1/2eNOS feed-forward mechanism", Proc. Natl. Acad. Sci., vol. 103, pp. 6530-6535 (2006).

Office Action issued in U.S. Appl. No. 12/224,384 dated Feb. 1, 2011.

Office Action issued in U.S. Appl. No. 12/224,384 dated Apr. 14, 2014.

Office Action issued in U.S. Appl. No. 12/224,384 dated Jul. 6, 2011.

Office Action issued in U.S. Appl. No. 12/224,384 dated Sep. 5, 2013.

Office Action issued in U.S. Appl. No. 12/224,384 dated Oct. 25, 2010.

Office Action issued in U.S. Appl. No. 14/486,124 dated Jan. 22, 2018.

Office Action issued in U.S. Appl. No. 14/486,124 dated Mar. 16, 2016.

Office Action issued in U.S. Appl. No. 14/486,124 dated Jul. 21, 2017.

Office Action issued in U.S. Appl. No. 14/486,124 dated Nov. 20, 2015.

(56) References Cited

OTHER PUBLICATIONS

Office Action issued in U.S. Appl. No. 14/486,124 dated Nov. 25, 2016.
Park et al., "The axonal attractant Netrin-1 is an angiogenic factor", Proc. Natl. Acad. Sci., vol. 101, pp. 16210-16215 (2004).
Rabizadeh, S. et al., "Induction of Apoptosis by the Low-Affinity NGF Receptor", Science, vol. 261, pp. 345-348 (1993).
Serafini, T. et al. "The Netrins Define a Family of Axon Outgrowth-Promoting Proteins Homologous to C. elegans UNC-6". Cell, vol. 78, Aug. 12, 1994, pp. 409-424.
Serafini, T. et al., "Netrin-1 is Required for Commissural Axon Guidance in the Developing Vertebrate Nervous System", Cell, vol. 87, pp. 1001-1014 (1996).
Serafini, T. et al., "The Netrins Define a Family of Axon Outgrowth-Promoting Proteins Homologous to C. elegans UNC-6", Cell, vol. 78, pp. 409-424 (2004).
Srinivasan, K. et al., Netrin-1/Neogenin Interaction Stabilizes Multipotent Progenitor Cap Cells during Mammary Gland Morphogensis, Dev. Cell, vol. 4, pp. 371-382 (2003).
Stein, E. et al., "Binding of DCC by Netrin-1 to Mediate Axon Guidance Independent of Adenosine A2B Receptor Activation", Science, vol. 291, pp. 1976-1982 (2001).
Stupack, D.G. et al., "Apoptosis of adherent cells by recruitment of caspase-8 to unligated integrins", J. Cell Biol., vol. 155, pp. 459-470 (2001).
Stupack, D.G. et al., "Potentiation of neuroblastoma metastasis by loss caspase-8", Nature, vol. 439, pp. 95-99 (2006).
Tanikawa, C. et al., "p53RDL1 regulates p53-dependent apoptosis", Nat. Cell Biol., vol. 5, pp. 216-223 (2003).
Thibert, C. et al., "Inhibition of Neuroepithelial Patched-Induced Apoptosis by Sonic Hedgehog", Science, vol. 301, pp. 843-846 (2003).
Thiebault, K. et al., "The netrin-1 receptors UNC5H are putative tumor suppressors controlling cell death commitment", Proc. Natl. Acad. Sci., vol. 100, pp. 4173-4178 (2003).
Wang, J.J. et al., "Dimerization-Dependent Block of the Proapoptotic Effect of p75NTR", J. Neurosci. Res., vol. 60, pp. 587-593 (2000).
Wilson, B.D. et al. "Netrins Promote Development and Therapeutic Angiogensis", Science, vol. 313, pp. 640-644 (2006).
Yang, X. et al., "Autoproteolytic Activation of Procaspases by Oligomerization", Molecular Cell, vol. 1, pp. 319-325 (1998).
Yebra, M. et al., "Recognition of the Neural Chemoattractant Netrin-1 by Integrins $\alpha 6\beta 4$ and $\alpha 3\beta 1$ Regulates Epithelial Cell Adhesion and Migration", Dev. Cell, vol. 5, pp. 695-707 (2003).

* cited by examiner

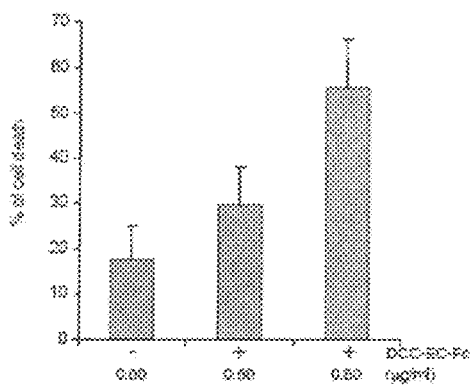 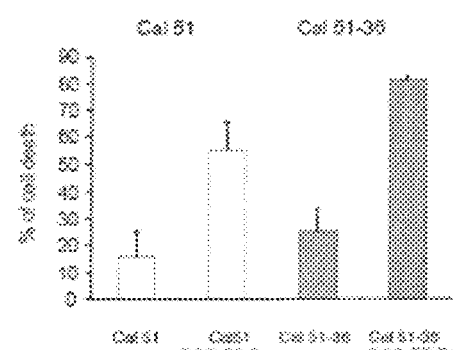
FIGURE 4A  FIGURE 4B
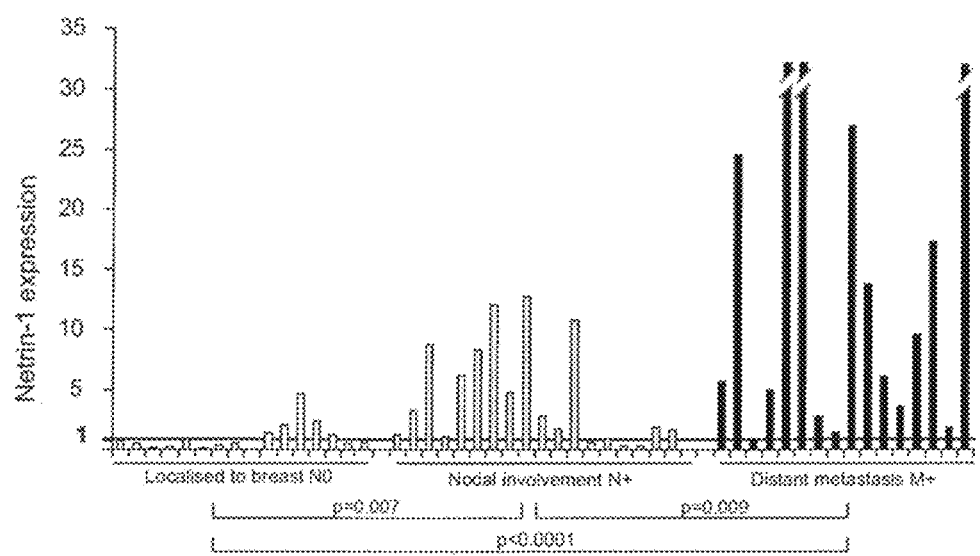
FIGURE 5

SCREENING FOR ANTI-CANCER COMPOUNDS USING NETRIN-1 ACTIVITY

The subject matter of the present invention relates to an in vitro method for the screening of anti-cancer compounds based on the capacity for these compound to interact with netrin-1 and/or to inhibit the dimerization of the intracellular domain of the netrin-1 receptor expressed in tumor cells. The invention also relates to a method for predicting the presence of metastatic cancer, or for determining the efficiency of an anti-cancer treatment based on the measuring of the expression level of netrin-1. The invention further comprises kits and compounds as a medicament for the treatment of metastatic cancer such as breast cancer, related to the overexpression of netrin-1 by the tumor ells.

Netrin-1, a diffusible laminin-related protein, has been shown to play a major role in the control of neutronal navigation during the development of the nervous system[31], by interacting with its main receptors, DCC (Deleted in Colorectal Cancer)[1, 2, 3] and UNC5H[4, 5]. However, more recently, netrin-1 has emerged as a completely different molecule that regulates cell survival. Indeed, the netrin-1 receptors DDC and UNC5H, —i.e., UNC5H1, UNC5H2, and UNC5H3—belong to the so-called dependence receptor family[6, 7]. Dependence receptors form a group of receptor that share the ability to induce cell death when expressed in settings in which their ligand is not available[44]. Such receptors, which also include RET[8], β-integrins[9], Patched[10], neogenin[11], p75[NTR 12] and the androgen receptor[40], share the functional property of inducing cell death when disengaged from their ligands, while the presence of their ligand blocks this pro-apoptotic activity. Such receptors thus create cellular states of dependence on their respective ligands[13, 14].

Thus dependence effect has been suggested to act as mechanism for eliminating tumor cells that would develop in settings of ligand unavailability, proliferation of tumor cells in a cell environment with constant and limited ligand presence or migration of metastatic tumor cells towards tissues where the ligand is not expressed. A selective advantage for a tumor cell would then be to lose the pro-apoptotic activity of its dependence receptors. It was predicted from genetic screens that the C. elegans netrin-1—UNC6—interacted with UNC40 and with UNC5[42]. Four orthologues of UNC5 were identified in mammals: UNC5H1, H2, H3, H4 and UNC40 was found to be the orthologue of the vertebrate DCC (Deleted in Colorectal Cancer)[39]. along this line, DCC was proposed in the early 1990s to be a tumor suppressor gene, whose expression is lost in the vast majority of human cancers[15, 16]. This hypothesis also fits with the recent observation that UNC5H genes are down-regulated in the vast majority of colorectal tumors, hence suggesting that the loss of UNC5H genes represents a selective advantage for tumor development[17]. Interestingly, in mice, both inactivation of UNC5H3 and overexpression of netrin-1 in the gastrointestinal tract are associated with intestinal tumor progression[18, 19], hence demonstrating per se that the loss of netrin-1 dependence receptors in the human pathology is a causal factor for tumor progression. However, although an initial series of reports supported the fact that DCC acted as a tumor suppressor (for a review see[29]), doubts have arisen, mainly because of the rarity of point mutations in the DCC coding sequence and because of the lack of tumor predisposition in DCC hemizygous mice[41].

However, the model described above predicts that both loss of the netrin-1 receptors and gain of ligand expression—i.e., autocrine expression—should be observed in human cancers, as they should represent similar selective advantages. This question is important not only for basic knowledge, but is crucial for therapy: indeed, inhibiting the extracellular interaction between netrin-1 dependence receptors and netrin-1 could represent an appealing strategy to trigger tumor regression.

It is particular desirable to provide simple and consistent means for identifying and characterizing new compounds which can be used for the treatment of cancer.

Surprisingly, the inventors have first demonstrated that, rather than losing netrin-1 dependence receptors, the majority of metastatic breast tumors show increased netrin-1 expression, a trait that may be used in therapy to trigger death of metastasic tumor.

If the pro-apoptotic signaling of DCC and/or UNC5H is beginning to be documented, an important question in this death/life signature dictated by DCC, UNC5H and more generally by the other known dependence receptors, is how does the presence of the ligand inhibit their pro-apoptotic activity[50].

In a second time, the inventors have analyzed whether netrin-1 induced DCC and/or UNC5H multimerization could be the critical step that inhibits DCC and/or UNC5H pro-apoptotic activity. Surprisingly, they have demonstrated that netrin-1 receptor, such as DCC and/or UNC5H multimerizes in response to netrin-1, a process sufficient to inhibit apoptosis.

In a first aspect, the present invention is directed to an in vitro method for selecting a compound for the prevention or the treatment of cancer, wherein said method comprises the following steps of:
a) having a medium containing netrin-1, or a fragment thereof, and a netrin-1 receptor, or a fragment thereof, wherein:
  said netrin-1, or a fragment thereof, and said netrin-1 receptor, or a fragment thereof, is able to specifically interact together to form a binding pair, and/or
  said netrin-1, or a fragment thereof, is able to induce the dimerization or multimerization of said netrin-1 receptor, or a fragment thereof, particularly the intracellular domain of said netrin-1 receptor;
b) contacting said medium with the compound to be tested;
c) —measuring the inhibition of the interaction between netrin-1, or a fragment thereof, and said netrin-1 receptor, or a fragment thereof, and/or
  determine whether said compound inhibit the dimerization or multimerization of said netrin-1 receptor, or a fragment thereof, particularly the dimerization of the intracellular domain of said netrin-1 receptor; and
d) selecting said compound if:
  the measuring in step c) demonstrates a significantly inhibition of the interaction between netrin-1, or a fragment thereof, and netrin-1 receptor, or a fragment thereof, in presence of said compound, and/or
  the determination in step c) demonstrates a significantly inhibition of the dimerization or multimerization of said netrin-1 receptor, or a fragment thereof, in presence of said compound, particularly the dimerization of the intracellular domain of said netrin-1 receptor.

By the terms interaction between netrin-1 and its netrin-1 receptor, it is intended to designate in the present application the interaction which result to the selective advantage for tumor cells to escape netrin-1 dependence receptors induced apoptosis, preferably due to elevated netrin-1 level.

So, the inhibition of this interaction can be obtained for example by the complete or partial inhibition of the binding of netrin-1 to its receptor, notably in presence of a competitive ligand (such as an antibody which is directed to this extracellular membrane domain of said netrin-1 receptor), or in presence of a compound able to form a specific complex with the netrin-1 (such as a soluble extracellular membrane domain of its netrin-1 receptor, or part thereof).

In a preferred embodiment, the method according to the present invention is characterized in that said cancer to be prevent or treated is a cancer wherein tumoral cells express or overexpress netrin-1.

In another preferred embodiment, the method according to the present invention is characterized in that said cancer to be prevent or treated is selected from the group consisting of breast cancer, colorectal cancer, lung cancer, neuroblastoma, glioma, acute myeloid leukemia, sarcoma, melanoma, ovarian adenocarcinoma, renal adenocarcinoma pancreatic adenocarcinoma, uterus adenocarcinoma, stomac adenocarcinoma, kidney adenocarcinoma and rectal adenocarcinoma.

In another preferred embodiment, the method according to the present invention is characterized in that said cancer to be prevent or treated is a metastatic or an aggressive cancer.

In the method according to the invention, said netrin-1 receptor is preferably selected from the group of DCC, UNC5H (particularly UNC5H1, UNC5H2 and UNC5H3), neogenin and the adenosine A2b, more preferably selected from the group of DCC, UNC5H1, UNC5H2 and UNC5H3.

In another preferred embodiment, the method according to the present invention is characterized in that at step a):
said netrin-1 receptor fragment comprises or is the extracellular domain of the netrin-1 receptor, or part thereof able to interact with netrin-1; and/or
said netrin-1 receptor fragment comprises or is the intracellular domain of the netrin-1 receptor, or part thereof able to dimerize or multimerize in presence of netrin-1.

In another preferred embodiment, the method according to the present invention is characterized in that said netrin-1 or/and said netrin-1 receptor are from mammal, particularly from mouse, rat or human.

In a particular aspect of the method of the present invention, at step a) said netrin-1 is from chicken.

In another preferred embodiment, the method according to the present invention is characterized in that said netrin-1 or/and said netrin-1 receptor and/or the compound to be tested is labelled by a marker able to be directly or indirectly measured.

In another preferred embodiment, the method according to the present invention is characterized in that at step c):
the measure of inhibition of the interaction between netrin-1, or a fragment thereof, and said netrin-1 receptor, or a fragment thereof, is carried out by immunoassay (particularly by ELISA or by Immunoradiometric Assay (IRMA)), by Scintillation Proximity Assay (SPA) or by Fluorescence Resonance Energy Transfer (FRET); and/or
the dimerization or multimerization, or its inhibition, of said netrin-1 receptor, or fragment thereof, particularly the intracellular domain, is carried out by immunoprecipitation or FRET.

In another particular preferred embodiment, the method according to the present invention is characterized in that at step a) said medium contains cells which express at their surface membrane an endogenous or a recombinant netrin-1 receptor particularly a recombinant extracellular domain of said netrin-1 receptor.

In another particular preferred embodiment, said recombinant netrin-1 receptor also comprises the intracellular domain of said netrin-1 receptor.

In another particular preferred embodiment, the method according to the present invention is characterized in that at step a) said medium contains tumoral cells, preferably metastatic tumoral cells, which express endogenously said netrin-1 receptor at their membrane surface and which express or overexpress netrin-1, and therein at step c) the inhibition of the interaction between netrin-1 and its netrin-1 receptor in presence of the compound to be tested, is measured by the apoptosis or cells death induced by the presence of the compound to be tested, preferably analysed using the trypan blue staining method as indicated in the examples below.

In a preferred embodiment said tumoral cells are selected from the group consisting of 4T1 cells, CAL51 cells, T47D cells, SKBR7 cells, IMR32 cells, GL26 cells and H358 cells, notably CAL51 cell lines, such as CAL51-36 cell lines, such as CAL51-36 cell line, which are much more susceptible to cell death in response to the presence of DCC-EC-Fc.

The present invention is also directed to an in vitro method for selecting a compound for the prevention or the treatment of cancer, wherein said method comprises the following steps of;
a) having a medium containing a mammal cell expressing an endogenous or a recombinant netrin-1 receptor, or a fragment thereof comprising at least its intracellular domain, preferably a tumor cell, more preferably a cell presenting dimerization or multimerization of its netrin-1 receptor intracellular domain or a cell wherein its netrin-1 receptor intracellular domain is able to dimerize or multimere in presence of netrin-1;
b) contacting said medium with the compound to be tested, optionally the medium further containing netrin-1, or a fragment thereof able to interact with the extracellular domain of the netrin-1 receptor;
c) determine whether the dimerization or multimerization of said netrin-1 receptor intracellular domain is inhibited in presence of said compound to be tested;
d) optionally, determine (for example by the blue trypan method) whether the presence of the compound to be tested induces the cell death of said mammal cell; and
e) selecting said compound if the determination in step c) demonstrates a significantly inhibition of the dimerization or multimerization of the intracellular domain of said netrin-1 receptor and/or if the determination in step d) demonstrates the cell death of said mammal cell.

In a second aspect, the present invention is directed to an in vitro method for predicting the presence of a metastatic cancer or an aggressive cancer (such as neuroblastome) in a patient having a primary tumor from a biopsy of said patient containing primary tumors cells, said method comprising the following step of:
(a) measuring of the netrin-1 expression level in said biopsy.

In a preferred embodiment, the method for predicting according to the present invention is characterized n that at step a) wherein an increase of the netrin-1 expression level in said biopsy, compared with expression of netrin-1 in on-metastatic primary tumor biopsies or in non-aggressive cancer biopsies is significant of the presence of a metastatic cancer or an aggressive cancer.

In a more preferred embodiment, the method for predicting according to the present invention is characterized in that a ratio superior to 2, preferably to 2.5, to 3, to 3.5, to 4, to 4.5 and to 5, between netrin-1 expression in the biopsy to be tested and in the non-metastatic or non-aggressive reference biopsy is significant of the presence of a metastatic or an aggressive cancer.

In a third aspect, the present invention is directed to an method for determining in vitro the efficiency of an anti-cancer treatment for a patient or for selecting patients who responds to a specific anti-cancer treatment, said method comprising the following step of:
(a) obtaining a primary tumor biopsy of said treated patient; and
(b) measuring of the netrin-1 expression level in said biopsy.
wherein the efficiency of said anti-cancer treatment is correlated with the decrease of the amount of the netrin-1 expression level measured in said biopsy, or
wherein the selected patients who respond to a specific anti-cancer treatment are patients where the amount of the netrin-1 expression level measured in their biopsy has been decreased after said specific treatment.

In a preferred embodiment, the method for determining in vitro the efficiency of an anti-cancer treatment for a patient or for selecting patients who respond to a specific anti-cancer treatment, is characterized in that said cancer induced an overexpression of netrin-1 and/or is a metastatic or an aggressive cancer.

In a preferred embodiment, the method for prediction or for determining in vitro the efficiency of an anti-cancer treatment for a patient is characterized in that the measured netrin-1 expression product is the RNA encoding netrin-1, particularly measured by a quantitative real time reverse PCR method, or in that the expression level of netrin-1 which is measured is the measure of the netrin-1 protein level, particularly by a method using specific antibodies able to specifically recognize said netrin-1 protein.

In a preferred embodiment, the method for prediction or for determining in vitro the efficiency of an anti-cancer treatment for a patient is characterized in that the primary tumor is a primary tumor of a cancer selected from the group consisting of breast cancer, colorectal cancer, lung cancer, neuroblastoma, glioma, acute myeloid leukemia, sarcoma, melanoma, ovarian adenocarcinoma, renal adenocarcinoma pancreatic adenocarcinoma, uterus adenocarcinoma, stomac adenocarcinoma, kidney adenocarcinoma and rectal adenocarcinoma.

In another aspect, the present invention is directed to a kit for the selection of a compound for the prevention or the treatment of cancer, wherein said kit comprises:
a netrin-1 receptor protein, or a fragment thereof able to specifically interact with the netrin-1 protein to form a binding pair, preferably recombinant protein; and
netrin-1 protein, or a fragment thereof able to specifically interact with said netrin-1 receptor protein to form a binding pair, preferably recombinant protein.

Said netrin-1 receptor being also preferably selected from the group of DCC, UNC5H (particularly UNC5H1, UNC5H2 and UNC5H3), neogenin and the adenosine A2b, more preferably selected from the group of DCC, UNC5H1, UNC5H2 and UNC5H3, more preferably from mammal such as from mouse, rat or human.

In a preferred embodiment, said kit comprises:
tumoral cells which express netrin-1 receptor and which express or overexpress netrin-1, particularly cells form metastatic tumoral cell line, preferably selected from the group consisting of 4T1 cells, CAL51 cells, T47D cells, SKBR7 cells, IMR32 cells, GL26 cells and H357 cells, notably CAL51 cell lines, such as CAL51-36 cell line, which are more susceptible to cell death in response to the presence of DCC-EC-Fc.

In another aspect, the present invention comprises a compound selected from the group consisting of:
a compound comprising an extracellular domain of netrin-1 receptor or fragment thereof able to specifically inhibit the interaction between the netrin-1 and said netrin-1 receptor, and/or able to inhibit the dimerization or multimerization of said netrin-1 receptor, or a fragment thereof, particularly to inhibit the intracellular domain of said netrin-1 receptor; and
a monoclonal or polyclonal antibody directed specifically against netrin-1 or netrin-1 receptor, particular directed to the extracellular domain of said netrin-1 receptor or to the netrin-1 fragment able to interact with the extracellular domain of said netrin-1 receptor,
as a medicament.

The amino acid sequence of human netrin-1 or human netrin receptor such as UNC5H1, UNC5H2 and UNC5H3 (Unc-5 homolog 1, 2 and 3 equivalent to Unc-5 homolog A, B and C) are well known by the skilled man. Example of these amino acid sequences with the localization of their particular domain can be found in Genbank under the accession number AAD09221 or NP_005813 for human netrin-1, NP_588610 for human netrin receptor Unc-5 homolog 1, Q8IZJI for netrin receptor Unc-5 homolog 2 and O95185 for Unc-5 homolog 3.

Preferably, in the compounds of the present invention, said extracellular domain of of netrin-1 receptor or fragment thereof is selected from the group of DCC, UNC5H (particularly UNC5H1, UNC5H2 and UNC5H1, UNC5H2 and UNC5H3, more preferably from mammal such as from mouse, rat or human.

In a more preferred embodiment, said compound according to the present invention comprises an extracellular domain of netrin-1 receptor from DCC, preferably said compound is DCC-EC-Fc or DCC-5Fbn.

In another aspect, the present invention pertains to the use of the level of netrin-1 expression as a marker for the identification of metastatic cancer in a patient, preferably of metastatic breast or colorectal cancer, the most preferred being the metastatic breast cancer.

In another aspect, the present invention pertains to a method of treatment for inducing the apoptosis or the cell death of tumor cells which have acquired the selective advantage to escape netrin-1 dependence receptors induced apoptosis, preferably by elevated netrin-1 level, in a patient comprising administering a compound able to inhibit the interaction between netrin-1 and its netrin-1 receptor, a compound able to inhibit the dimerization or the multimerization of the netrin-1 receptor, a compound according to the present invention, or selected by the method of the present invention, in said patient in need thereof.

In another aspect, the present invention pertains to a method for the prevention or for the treatment of cancer in a patient comprising administering a compound according to the present invention, or selected by the method of the present invention, in said patient in need thereof.

The present invention also comprises the use of a compound according to the present invention, or selected by the method of the present invention, for the manufacture of a medicament for the prevention or the treatment of cancer in mammals, including man. Preferably said cancer is a metastatic or an aggressive cancer.

More preferably, in the method of treatment or in the use of a compound according to the present invention, said cancer is selected from the group consisting of breast cancer, colorectal cancer, lung cancer, neuroblastoma, glioma, acute myeloid leukemia, sarcoma, melanoma, ovarian adenocarcinoma, renal adenocarcinoma pancreatic adenocarcinoma, uterus adenocarcinoma, stomac adenocarcinoma, kidney adenocarcinoma and rectal adenocarcinoma.

More preferably, in the method of treatment or in the use of a compound according to the present invention, the primary tumor cells of said cancer express or overexpress netrin-1.

The term "antibody" as used herein refers to immunoglobulin molecules and immunologically active portions of immunoglobulin molecules, i.e., molecules that contain an antigen binding site which specifically binds (immunoreacts with) the netrin-1 protein or its receptor.

The term "antibody" comprises monoclonal or polyclonal antibodies but also chimeric or humanized antibodies.

An isolated netrin-1 protein or netrin-1 receptor protein, or a specific fragment thereof can be used as immunogen to generate antibodies that bind such protein using standard techniques for polyclonal and monoclonal antibody preparation. It may be also possible to use any fragment of these protein which contains at least one antigenic determinant may be used to generate these specific antibodies.

A protein immunogen typically is used to prepare antibodies by immunizing a suitable subject, (e.g., rabbit, goat, mouse or other mammal) with the immunogen. An appropriate immunogenic preparation can contain said protein, or fragment thereof, and further can include an adjuvant, such as Freund's complete or incomplete adjuvant, or similar immunostimulatory agent.

Thus, antibody for use in accordance with the invention include either polyclonal, monoclonal chimeric or humanized antibodies, antibodies able to selectively bind, or which selectively bind to an epitope-containing a polypeptide comprising a contiguous span of at least 8 to 10 amino acids of an amino acid sequence of the netrin-1 protein or its receptor.

A preferred agent for detecting and quantifying MRNA or cDNA encoding netrin-1 protein, is a labeled nucleic acid probe or primers able to hybridize this mRNA or cDNA. This nucleic acid probe can be an oligonucleotide of at least 10, 15, 30, 50 or 100 nucleotides in length and sufficient to specifically hybridize under stringent conditions to the mRNA or cDNA. The nucleic acid primer can be an oligonucleotide of at least 10, 15 or 20 nucleotides in length and sufficient to specifically hybridize under stringent conditions to the mRNA or cDNA, or complementary sequence thereof.

A preferred agent for detecting and quantifying the netrin-1 protein, is an antibody able to bind specifically to this protein, preferably an antibody with a detectable label. Antibodies can be polyclonal, or more preferably, monoclonal. A intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

For example, in vitro techniques for detection of candidate mRNA include Northern hybridization and in situ hybridizations. In vitro techniques for detection of the candidate protein include enzyme linked immunosorbent assays (ELISAs), Western blots, immunoprecipitations and immunofluorescence. In vitro techniques for detection of candidate cDNA include Southern hybridizations.

When the invention encompasses kits for quantifying the level of netrin-1 protein, the kit can comprise a labeled compound or agent capable of quantifying these proteins. Said agents can be packaged in a suitable container. The kit can further comprise instructions for using the kit to quantify the level of the netrin-1 protein or of the netrin-1 transcript.

In certain embodiments of the method of the present invention, the determination of the netrin-1 transcripts involves the use of a probe/primer in a polymerase chain reaction (PCR), such as anchor PCR or RACE PCR, or, alternatively, in a ligation chain reaction (LCR) (see, e.g., Landegran et al., 1988, Science 241:23-1080; and Nakazawa et al., 1994, Proc. Natl. Acad. Sci. USA, 91:360-364), or alternatively quantitative real time RT-PCR This method can include the steps of collecting a sample of cells from a patient, isolating nucleic acid (e.g. m/RNA) from the cells of the sample, optionally transforming mRNA into corresponding cDNA, contacting the nucleic acid sample with one or more primers which specifically hybridize to the netrin-1 or mRNA or their corresponding cDNA under conditions such that hybridization and amplification of the netrin-1 mRNA or cDNA occurs, and quantifying the presence of the amplification products. It is anticipated that PCR and/or LCR may be desirable to use as an amplification step in conjunction with any of the techniques used for quantifying nucleic acid detecting.

The methods described herein may be performed, for example, by utilizing pre-package diagnostic kits comprising at least one probe nucleic acid or set of primer of antibody reagent descried herein, which may be conveniently used, e.g., in clinical settings to follow-up or diagnose patients.

Finally, the present invention is related to the use of antisense or iRNA (interfering RNA) oligonucleotides specific of the nucleic acid encoding netrin-1 protein for the manufacture of a medicament indented to prevent or to treat metastatic or aggressive cancer, preferably said cancer is selected from the group consisting of breast cancer, colorectal cancer, lune cancer, neuroblastoma, glioma acute myeloid leukemia, sarcoma, melanoma, ovarian adenocarcinoma, renal adenocarcinoma pancreatic adenocarcinoma, uterus adenocarcinoma, stoma adenocarcinoma, kidney adenocarcinoma and rectal adenocarcinoma.

Interfering RNA (iRNA) is a phenomenon in which a double stranded RNA (dsRNA) specifically suppresses the expression of a gene bearing its complementary sequence. iRNA has since become a useful research tool for many organisms. Although the mechanism by which dsRNA suppresses gene expression is not entirely understood, experimental data provide important insights. This technology has great potential as a tool to study gene function in mammalian cells and may lead to the development of pharmacological agents based up siRNA (small interfering RNA).

When administered to a patient, a compound of the present invention is preferably administered as component of a composition that optionally comprises a pharmaceutically acceptable vehicle. The composition can be administered orally, or by any other convenient route, and may be administered together with another biologically active agent. Administration can be systemic or local. Various delivery systems are known, e.g., encapsulation in liposomes, microparticles, microcapsules, capsules, etc., and can be used to administer the selected compound of the present invention or pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, rectally, by inhalation, or topically. The mode of administration is left to the discretion of the practitioner. In most instances, administration will result in the release of the compound into the bloodstream or directly in the primary tumor.

Compositions comprising the compound according to the invention or selected by the methods according to the present invention, form also part of the present invention. These compositions can additionally comprise a suitable amount of a pharmaceutically acceptable vehicle so as to provide the form for proper administration to the patient. The term "pharmaceutically acceptable" means approved by a regulatory agency or listed by a national or recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gelatin, starch and the like. In addition, auxiliary, stabilizing, thickening, lubricating and coloring agents may be used. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, sodium stearate, glycerol monostearate, sodium chloride, dried skim milk, glycerol, propylene, glycol, water and the like. Test compound compositions, if desired, can also contain minor amounts of wetting or emulsifying agents, or pH buffering agents. The compositions of the invention can take the form of solutions, suspensions, emulsion, tables, pills, pellets, capsules, capsules containing liquids, powders, sustained-release formulation, suppositories, emulsions, aerosols, sprays, suspensions, or any other from suitable for use. Said composition is generally formulated in accordance with routing procedures as a pharmaceutical composition adapted to human beings for oral administration or for intravenous administration. The amount of the active compound or a that will be effective in the treatment can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of the practitioner and each patient's circumstances. However, suitable dosage ranges for oral, intranasal, intradermal or intravenous administration are generally about 0.01 milligram to about 75 milligrams per kilogram body weight per day, more preferably about 0.5 milligram to 5 milligrams per kilogram body weight per day.

It is to be understood that while the invention has been described in conjunction with the above embodiments, that the foregoing description and the following examples are intended to illustrate and not limit the scope of the invention. Other aspects, advantages and modifications within the scope of the invention will be apparent to those skilled in the art to which the invention pertains.

FIGURE LEGENDS

Figure 1B:
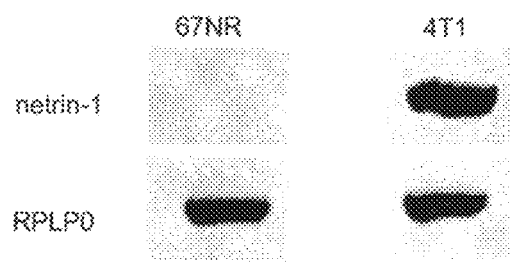

FIGS. 1A and 1B: Netrin-1 is over-expressed in human metastatic breast tumors

FIG. 1A: Expression profile of netrin-1 examined with quantitative real time reverse transcription PCR. Q-RT PCR was performed using total RNA extracted from 15 metastatic (solid bar) and 15 non-metastatic (open bar) primary tumor biopsies with specific human netrin-1 primers[26] and primers corresponding to the human TBP gene (TATA Binding Protein). TBP was used as a control here, as it shows a weak variability at the mRNA level between normal and breast tumoral tissues, as described in[25]. Netrin-1 expression is given as the ratio between netrin-1 expression in each sample and the average of netrin-1 expression in the non-metastatic samples.

FIG. 1B: Q-RT-PCR was performed using total RNA extracted from 67NR and 4T1 mouse cell lines with specific mouse netrin-1 primers and the mouse gene RPLP0 as standard.

Figure 2A:
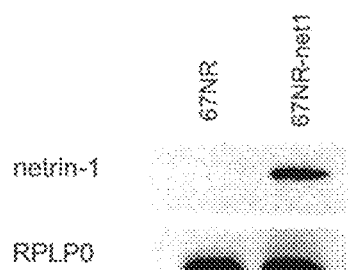
Figure 2B:
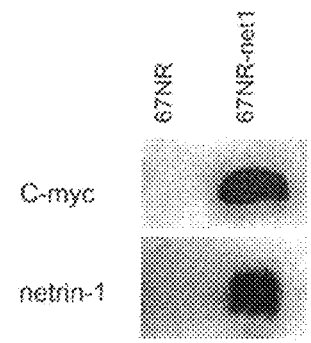

FIGS. 2A-2D: Forced expression of netrin-1 in 67NR mouse cell line leads to metatasis development FIGS. 2A and 2B: Mock transfected 67NR cells or 67NR cells stably transfected with netrin-1 (67NR-net) were submitted to netrin-1 expression analysis. FIG. 2A, RT-PCR using specific chicken netrin-1 primers was performed using total RNA extracted from 67NR-net1 and 67NR-mock. FIG. 2B, Western blot using anti-myc (chick netrin-1) or anti-netrin-1 antibodies was performed.

Figure 2C:
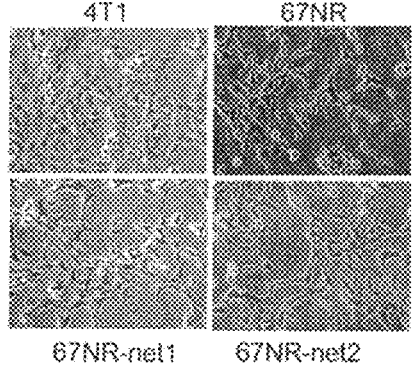

FIG. 2C: Photomicrographs of the two 67NR-net1 and 67NR-net2 clones compared to parental 67NR and to 4T1 cell line.

Figure 2D:
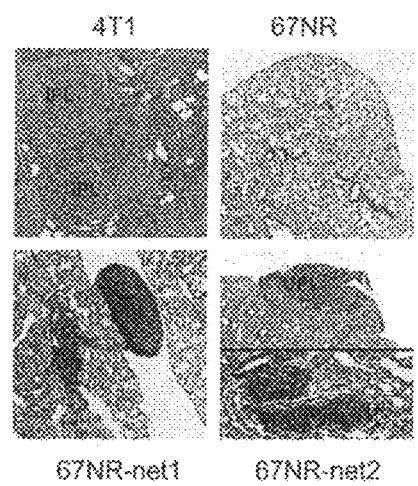

FIG. 2D: Metastatic 4 T1 cells, two control cell clones bearing puromycine resistance (67NR1 and 67NR2) and two netrin-1 expressing cell clones (67NR-net1 and 67NR-net2) were injected in fat pad of 16 mice (4 mice per cell type) and metastasis was analyzed in the lung environment. Representative photomicrographs of under pleural and intra-parenchymatous nodules after injection of the respective cell clones (4T1, 67NR1, 67NRnet1, 67NRnet2). IPL: intra-parenchymatous lesion, UPL: under-pleural lesions.

FIGS. 3A-3D: Induction of mouse metastatic cell death by inhibiting the netrin-1/receptor interaction FIG. 3A: Scheme representing netrin-1 and its receptors, DCC and UNC5H.

Figure 3A:
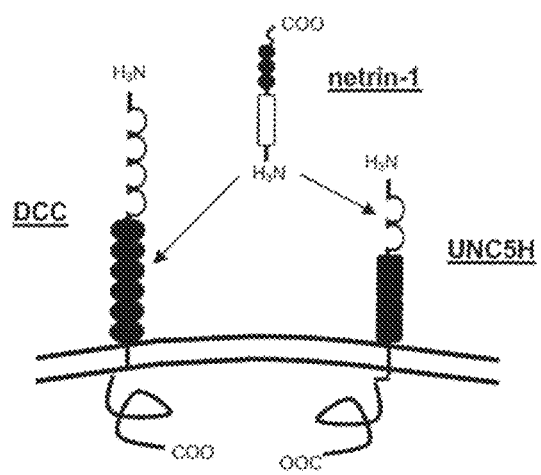
Figure 3B:
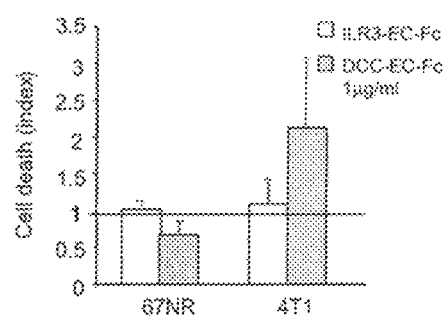
Figure 3C:
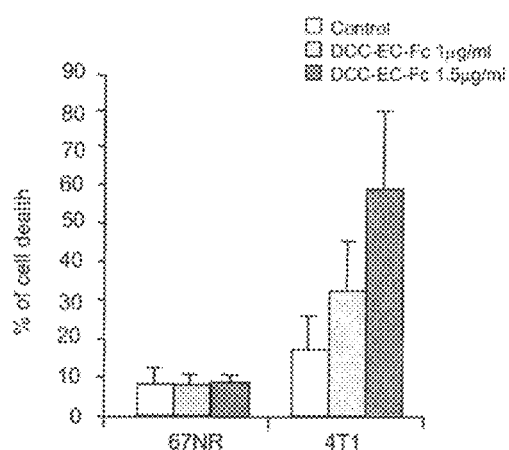
Figure 3D:
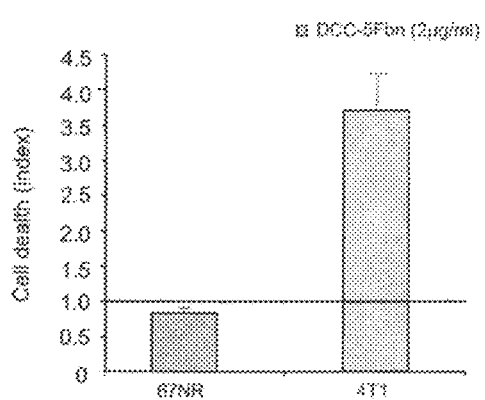

FIGS. 3B, 3C, 3D: Quantitative analysis of cell death in 67NR and 4T1 cells using either DCC-EC-Fc and non specific IL3-EC-Fc as a control (FIG. 3B), at different concentration (FIG. 3C) or the more restricted DCC-5Fbn domain (FIG. 3D) as a competitor for netrin-1/receptor interaction. Cell death was quantified either by the trypan blue exclusion assay (FIGS. 3B, 3D) or by caspase activity assay (FIG. 3C). Standard deviations are indicated (n=3).

FIGS. 4A and 4B: Induction of human metastatic cell death by inhibiting netrin-1/receptor interaction FIG. 4A: quantitative measurement of CAL51 cell death treated with different concentration of DCC EC-Fc by the trypan blue exclusion assay.

FIG. 4B: Quantitative analysis of cell death monitored by trypan blue exclusion in the CAL51 parental cell line or in the clonal cell line CAL51-36, treated or not with the DCC-EC-Fc competitor in culture media.

FIG. 5: Netrin-1 is over-expressed in human metastatic breast tumors

Expression profile of netrin-1 examined with quantitative real time reverse transcription PCR, Q-RT PCR was performed using total RNA extracted from 51 tumor biopsies. They were obtained from patient with tumors localized to the breast (N0, empty bar); with only axillary node involvement (N+, gray bar) and with distant metastases at diagnosis (M+, solid bar). Specific human netrin-1 primers[39] and primers corresponding to the human PBGD gene (TATA Binding Protein) were used. PBGD was used as a reference here, as it shows a weak variability at the mRNA level between normal and breast tumoral tissues, as it shows a weak variability at the mRNA level between normal and breast tumoral tissues, as described in[38]. The other reference TBP was also used with similar results (not shown). Netrin-1 expression is given as the ratio between netrin-1 expression in each sample and the average of netrin-1 expression in the N0 samples. A non parametric statistical significance test (Mann-Whitney) was used, the p value is indicated.

Figure 6A:
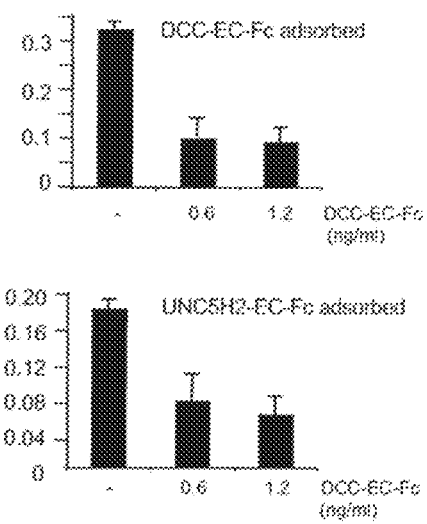
Figures 6B, 6C:
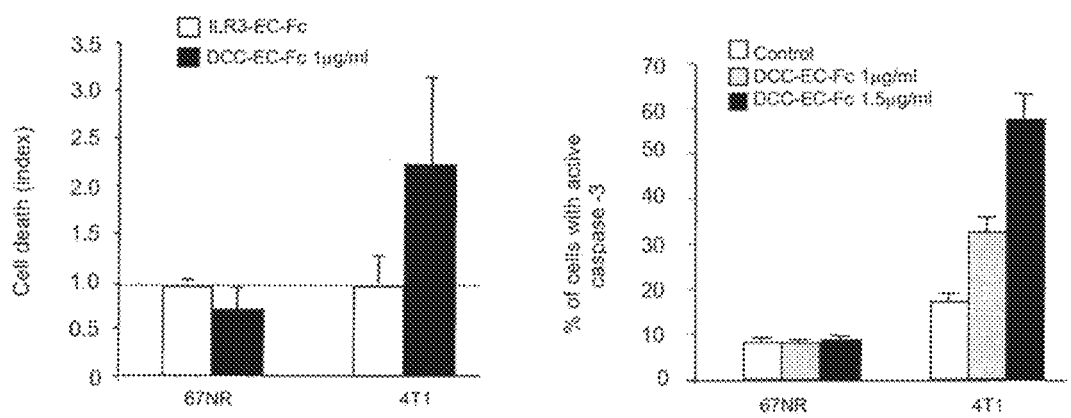

FIGS. 6A-6C: Induction of metastatic cell death by inhibiting the netrin-1/receptor interaction FIG. 6A: DCC-EC-Fc displaces DCC/netrin-1 and UNC5H2/netrin-1 interaction. ELISA assay with DCC-EC-Fc (top panel) or UNC5H2-EC-Fc (bottom panel) coated, and quantification of bound netrin-1 using anti-netrin-1 antibody in the presence of increasing concentration of DCC-EC-Fc.

FIGS. 6B and 6C: Quantitative analysis of cell death in 67NR and 4T1 cells using either DCC-EC-Fc and non specific IL3-EC-Fc as a control. Cell death was quantified either by the trypan blue exclusion assay (FIG. 6B), or by caspase activity assay (FIG. 6C). Standard deviations are indicated (n=3).

Figure 7A:
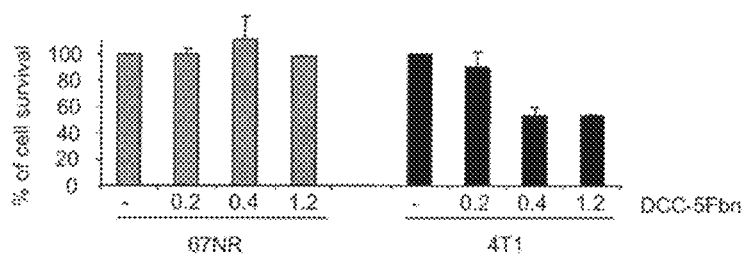
Figure 7B:
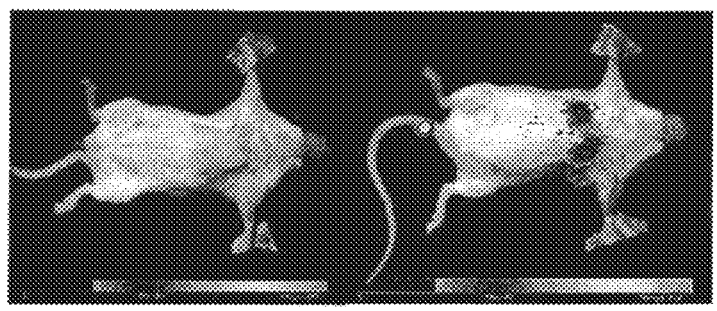
Figure 7C:
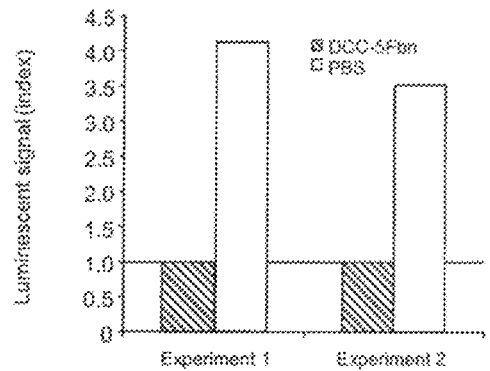

FIGS. 7A-7C: Inhibition of metastasis formation in mice by DCC-5Fbn treatment

FIG. 7A: Quantitative analysis of cell death in 67NR and 4T1 cells treated with DCC-5Fbn. MTT assay was performed on 67NR or 4T1 cells after treatment with increasing doses of DCC-5Fbn (μg/ml). Percentage of cell survival is presented. Standard deviations are indicated (n=3).

FIGS. 7B and 7C: 4T1-luc cells were i.v. injected in BALB/c mice at day 0 and PBS or DCC-5Fbn were injected every two days, once i.v., once i.p. starting at day 0. After 13 days, metastasis development was studied by luminescence recording (FIGS. 7B, 7C) or by examination of lungs under a scope.

FIG. 7B: A representative image of luminescence recording of PBS treated (right) or DCC-5Fbn treated (left) mice.

FIG. 7C: Quantification of the luminescence signal measured by the NightOwLB system. The number of photon/pixel/sec was quantified in each animal and an index of luminescent signal is given at the ratio between the average photo/mouse in PBS treated mice to the average signal detected in DCC-5Fbn treated mice. Two independent experiments are presented (20 mice were analyzed in experiment 1, 8 mice in the experiment 2).

A representative macroscopic photograph of a lung from PBS treated mice or from DCC-5Fbn treated mice has been made (not shown) can be demonstrated in the lung from PBS treated mice.

Figure 8A:
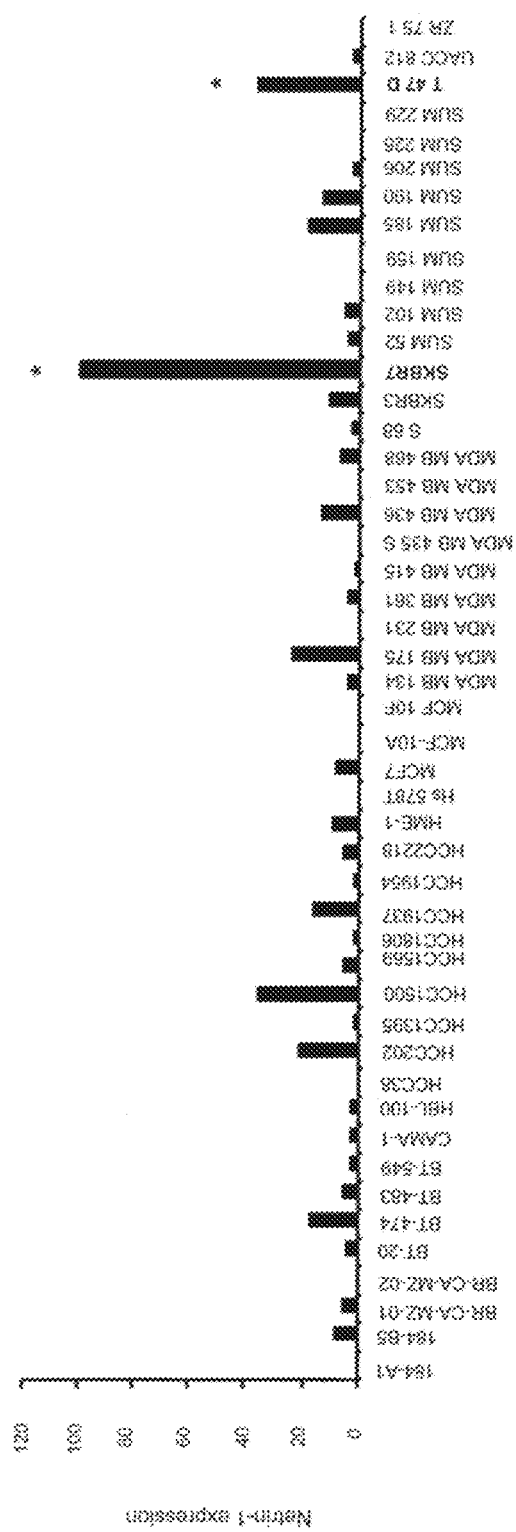
Figure 8B:
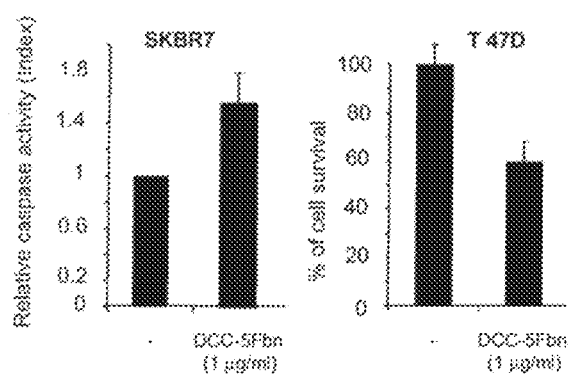

FIGS. 8A and 8B: Effect of DCC-5Fbn on netrin-1 expressing human cancer breast cell lines FIG. 8A: expression of netrin-1 examined by Q-RT PCR using total RNA extracted from 48 different breast tumor cell lines. Netrin-1 expression is given as the ratio between netrin-1 expression and the housekeeping gene HMBS expression (Hydroxymethylbilane synthase) in each sample. TBP was also used as a control here and give similar results. The two cell lines that have been selected for their high level of netrin-1 are indicated by stars.

FIG. 8B: Cell death induction by DCC-5Fbn in SKBR7 and T47D cell lines. Cell death was quantified either by MTT assay as described in FIG. 4A (right panel) or by caspase activity measurement as described in FIG. 3D (left panel). Standard deviations are indicated (n=3).

Figure 9A:
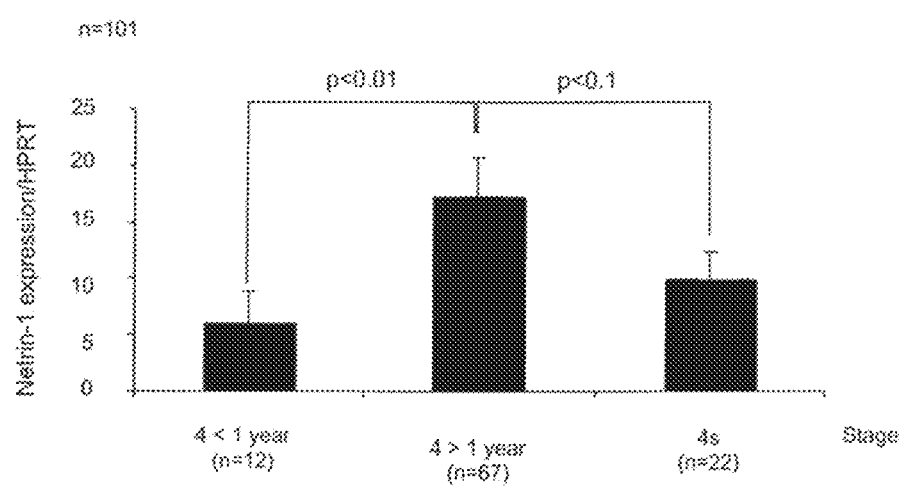
Figure 9B:
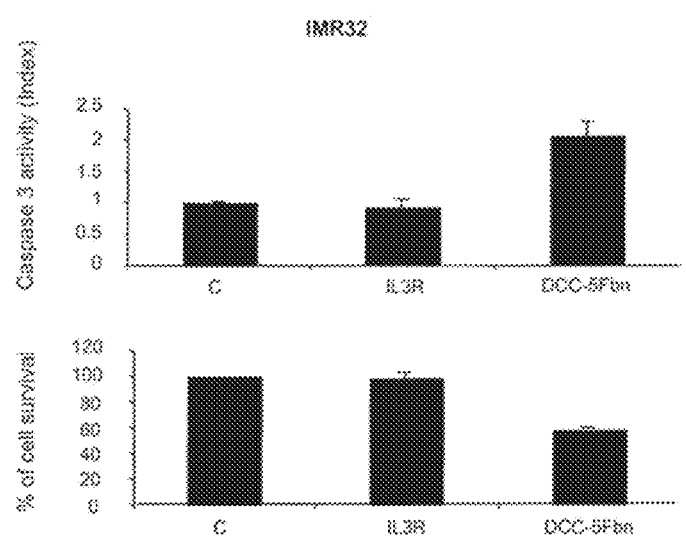

FIGS. 9A and 9B: Human neuroblastoma

FIG. 9A: Netrin-1 is a marker of aggressiveness in human neuroblastoma. Expression profile of netrin-1 examined with quantitative real time reverse transcription PCR. Q-RT PCR was performed sing total RNA extracted from 101 stage 4 or 4s neuroblastoma biopsies. Tumors were either stage 4 diagnosed in patient who were less than one year old (4<1 year) or stage 4 diagnosed in patient who were more than one year old (4>1 year). It can be noted that bad prognosis cancers (stage 4>1 year) show a significant overexpression of netrin-1. Student t tests were used and the p values are indicated.

FIG. 9B: IMR32 cells that endogenously produce netrin-1 were treated or not with DCC-5Fbn or as a control ILR3 (the interleukin-3 receptor ectodomain) and were reanalyzed for cell death either by measuring caspase activity (top) or by measuring cell survival via a MTT assay (down). Note that while IL3R has no effect on the death of IMR32 cells, DCC-5Fbn induces a significant IMR32 cell death. Standard deviations are indicated (n=3).

Figure 10A:
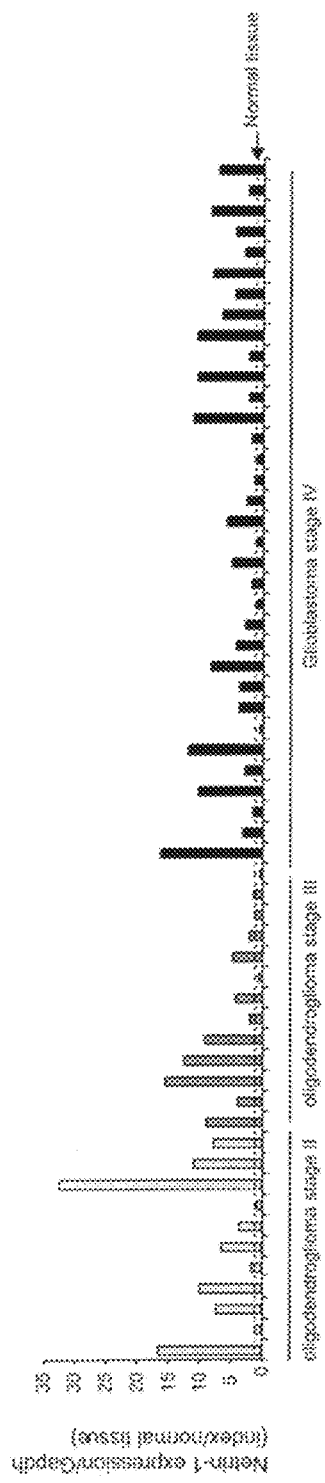
Figure 10B:
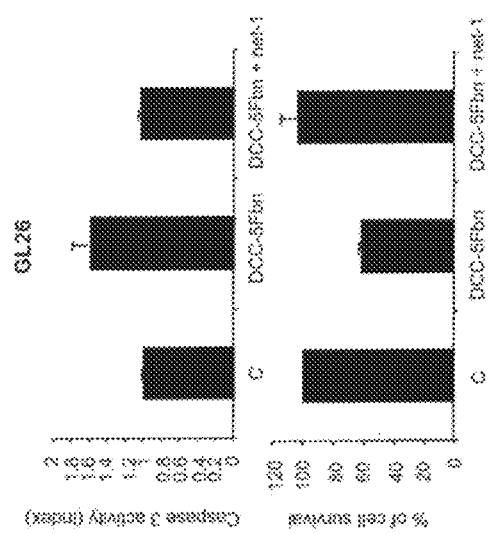

FIGS. 10A and 10B: Glioma

FIG. 10A: Netrin-1 is overexpressed in a large fraction of glioma. Expression profile of netrin-1 examine with quantitative real time reverse transcription PCR. Q-RT PCR was performed using total RNA extracted from stage II and stage III oligodendroglioma and stage IV glioblastoma biopsies and was compared to normal human brain.

FIG. 10B: GL26 cells that endogenously produce netrin-1 (not shown) were treated or not with DCC-5Fbn in the presence or not of an excess amount of recombinant netrin-1 and were analyzed for cell death either by measuring caspase activity (top) or by measuring cell survival via a MTT assay (down). Note that DCC-5Fbn induces a significant GL26 cell death and that this effect is fully inhibited by addition of netrin-1, thus demonstrating that the DCC-5Fbn effect is directly related to inhibition of endogenous netrin-1. Standard deviations are indicated (n=3).

Figure 11A:
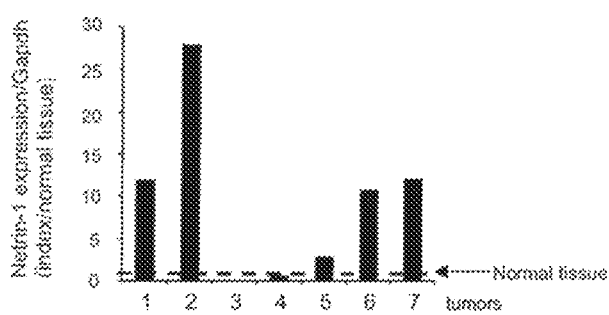
Figure 11B:
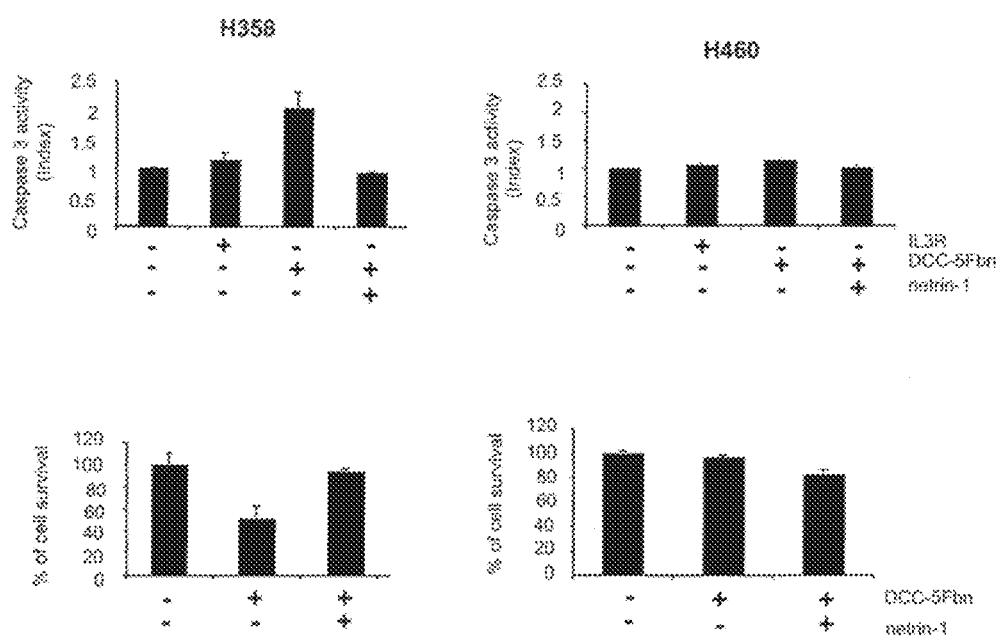
Figure 11C:
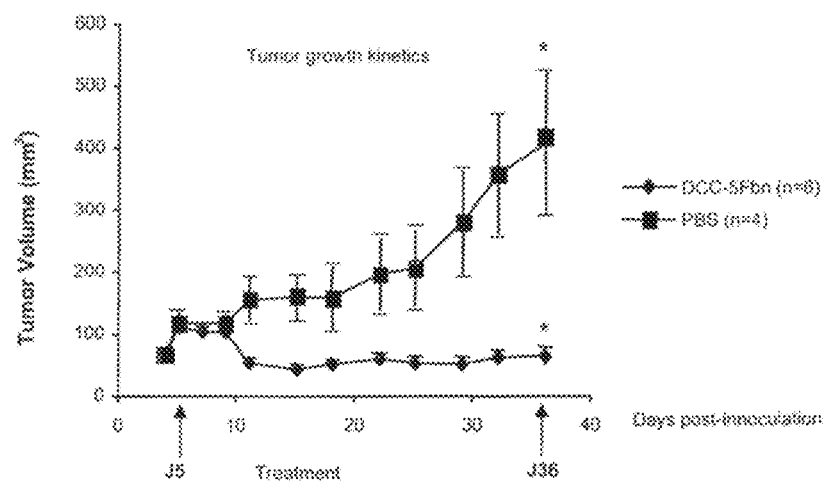

FIGS. 11A-11C: Lung cancer

FIG. 11A: Netrin-1 is overexpressed in a sizeable fraction of human lung cancer. Expression profile of netrin-1 examine with quantitative real time reverse transcription PCR. Q-RT PCR was performed using total RNA extracted from lung cancer biopsies and was compared to normal tissue.

FIG. 11B: H358 and H460, two NSCLC cell lines, were further used for cell death assays. H358 cells that endogenously express netrin-1 and H460 cells that fail to show detectable netrin-1 expression were treated or not with DCC-5Fbn in the presence or not of an excess amount of recombinant netrin-1 and were analyzed for cell death either by measuring caspase activity (top) or by measuring cell survival via a MIT assay (down). Note that DCC-5Fbn induces a significant H358 cell death but fails to show an effect on H460 cells. Moreover the death effect observed in H358 cells is fully inhibited by addition of netrin-1. Together with the fact that H460 cells are not sensitive to DCC-5Fbn, these data support that netrin-1 expressing lung tumor cells undergo apoptosis in response to DCC-5Fbn-.Standard deviations are indicated (n=3).

FIG. 11C: DCC-5Fbn inhibits xenografted H358 tumor growth in nude mice. Five-week old (20-22 g body weight) female athymic nu/nu mice were obtained from Charles River. The mice were housed in sterilized filter-topped cages and maintained in a pathogen-free animal facility. H358 cells were implanted by s.c. injection of $5 \cdot 10^6$ cells in 200 μL of PBS into the left flank of the mice. When tumors were established, PBS or 20 μg of DCC-5Fbn were administered into the tumor (i.t.) everyday (duration of treatment is indicated by arrows). Tumor sizes were measured by a calliper during 41 days. The tumor volume was calculated with the formula v=(0.5*(length*width$^2$))±SE,*) on 6 mice treated with DCC-5Fbn and 4 mice treated with PBS. Note that while PBS treated tumors were shown to grow, DCC-5Fbn treated tumors showed a massive regression.

Figure 12A:
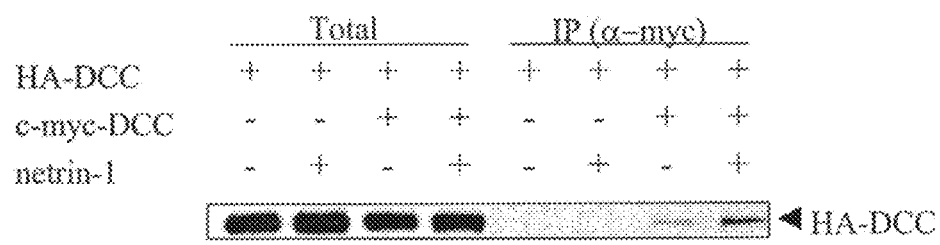
Figure 12B:
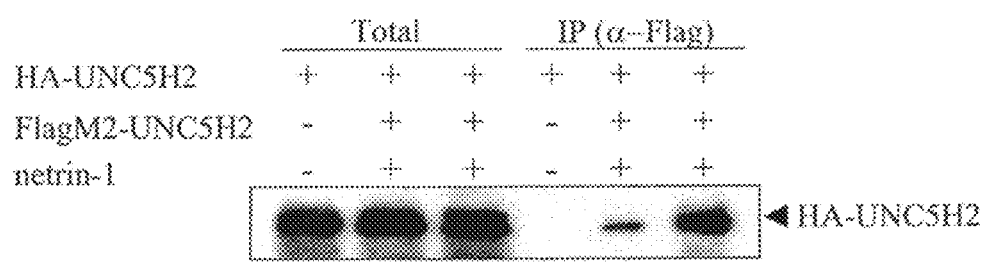

FIGS. 12A and 12B: Netrin-1 mediates DCC and UNC5H2 multimerization

FIG. 12A: DCC multimerization in the presence of netrin-1 in HEK293T cells. Lysates of HEK293T cells transiently transfected with HA-DCC and/or c-myc-DCC expressing constructs together or not with netrin-1 expressing construct were subjected to myc pull-down (IP α-myc). DCC-HA presence was revealed with an anti-HA antibody.

FIG. 12B: UNC5H2 dimerization in the presence of netrin-1 in HEK293T cells. Cell transfection and cell lysate preparation were done as in (A) but with HA-Unc5H2 and/or FlagM2-UNC5H2 expressing constructs. Cell lysates were subjected to Flag M2 pull-down (IP α-Flag). HA-UNC5H2 presence was revealed with an anti-HA antibody. Total: Western blot on lysate before pull-down.

Figure 13A:
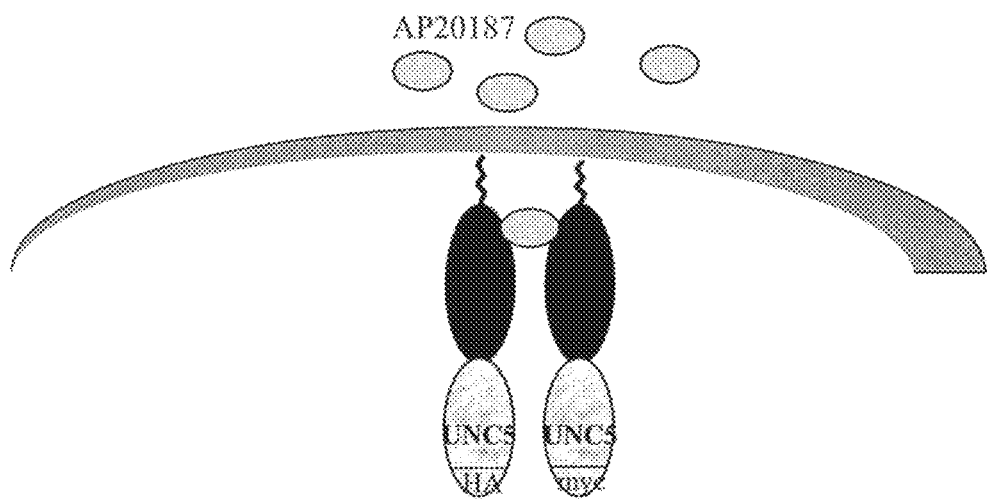
Figure 13B:
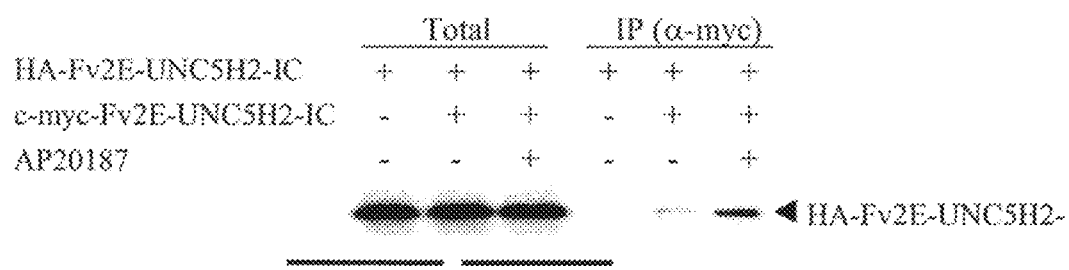

FIGS. 13A and 13B: Validation of the chemically-inducible system for UNC5H2 dimerization FIG. 13A: Schematic representation of Fv2e-UNC5H2 fusion constructions showing the two constructs (one tagged HA, the other one tagged c-myc) used to validate the artificial dimerization system.

FIG. 13B: Lysates of HEK293T cells transiently transfected with Fv2E-UNC5H2 tagged HA or c-myc with or without the dimerization drug (AP20187) were subjected to c-myc pull-down (IP α-myc). Total: Western blot on lysate before pull-down. HA-Fv2E-UNC5H2 presence was revealed with anti-HA antibody.

Figure 14A:
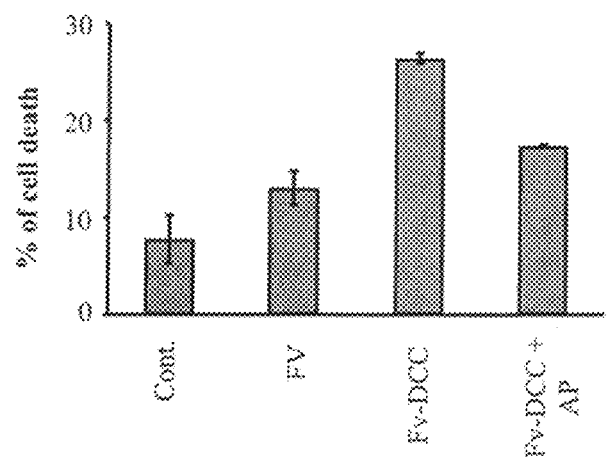
Figure 14B:
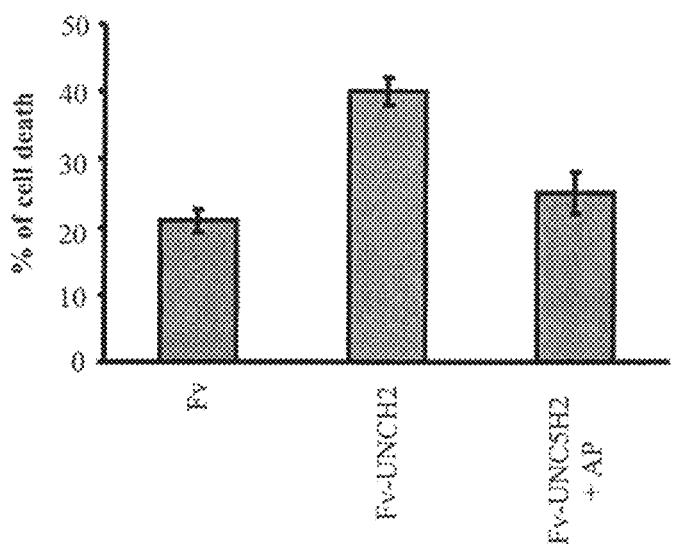
Figure 14C:
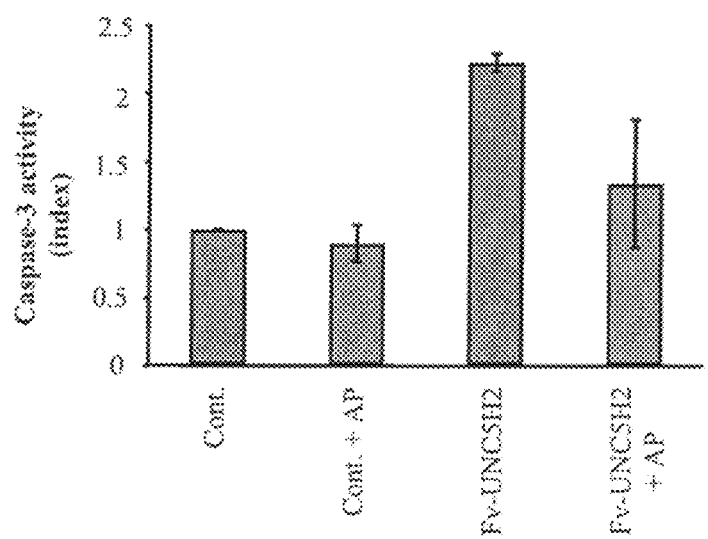

FIGS. 14A-14C: Forced DCC dimerization blocks its proapoptotic activity

FIG. 14A: DCC-induced cell death is inhibited by dimerization induced by AP20187, as measured by trypan blue exclusion. HEK293T cells were transfected with mock plasmid (Cont.), Fv2E (Fv), Fv2E-DCC-IC (Fv-DCC) with or without AP20187 (AP). In an conditions, cells were also transfected with the surface marker pKk. Transfected cells expressing the marker were magnetically labeled with MACSelect Microbeads and separated using a MACS Separator and Separation Columns. Trypan blue exclusion was assayed on these purified cells.

FIG. 14B: UNC5H2-induced cell death is inhibited by dimerization induced by AP20187, as measured by trypan blue exclusion as in (A). Cells were transfected with pMACSKk and Fv2E (Fv), Fv2E-UNC5H2-IC (Fv-UNC5H2) with or without AP20187 (AP).

FIG. 14C: UNC5H2-induced caspase activation is inhibited by dimerization induced by AP20187, as measured by relative caspase-3 activity. HEK293T cells were transfected with mock vector pCMV (Cont.), Fv2E (Fv), Fv2E-UNC5H2-IC (Fv-UNC5H2) with or without AP20187 (AP). Index of relative caspase activity is presented as the ratio between the caspase activity of the sample and that measured in HEK293T cells transfected with pCMV. Standard deviations are indicated (n=3).

Figure 15A:
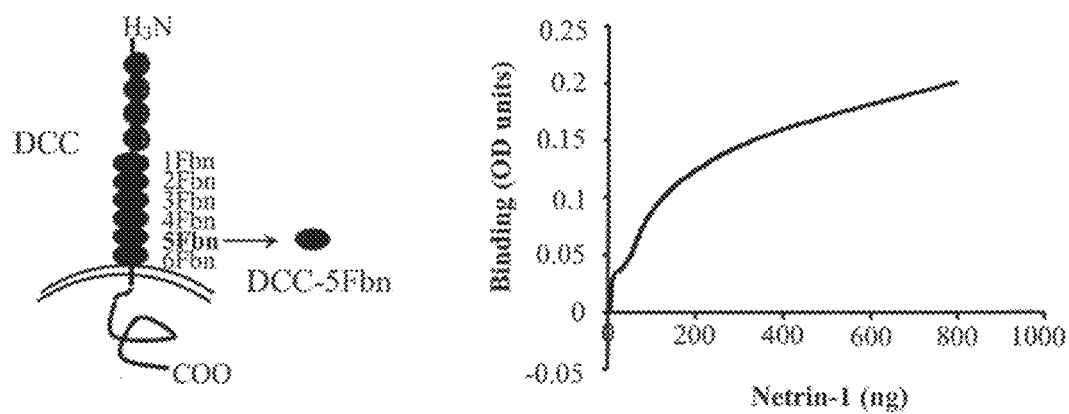
Figure 15B:
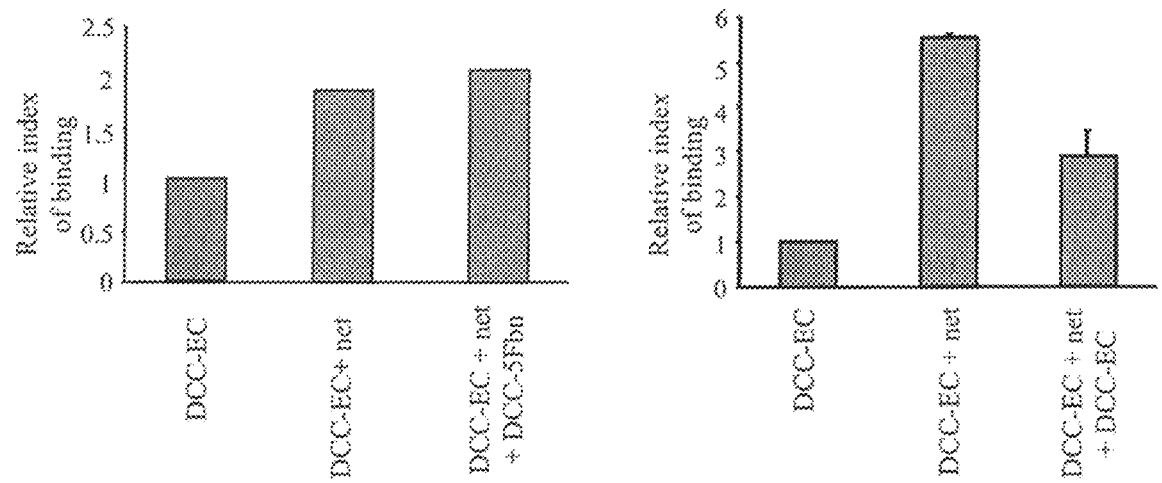
Figure 15C:
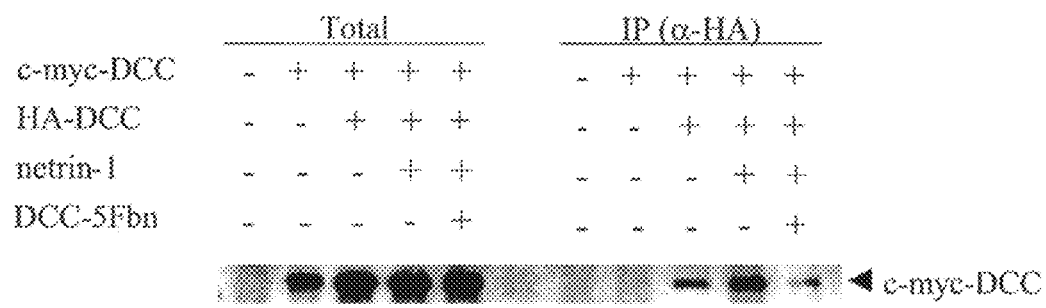

FIGS. 15A-15C: The recombinant soluble fifth fibronectin domain of DCC (DCC-5Fbn) inhibits netrin-1-induced DCC-multimerization FIG. 15A: Affinity curve of netrin-1 on DCC-5Fbn measured by ELISA test shows that DCC-5Fbn is able to bind netrin 1. DCC-5Fbn (100 ng) or IL3-R (600 ng) was coated and increasing doses of netrin-1 were added (0 to 800 ng). The IL-3 values were subtracted to the DCC-5Fbn values. The approximate Kd of DCC-5Fbn/netrin-1 was estimated at 5 nM.

FIG. 15B: Competition assay. As in (A) but the complete extracellular domain of DCC (DCC-EC, 125 ng) was coated instead of DCC-5Fbn and netrin-1 was added (50 ng) in the presence of either DCC-5Fbn (625 ng) or the complete DCC-EC (125 ng). Note that DCC-5Fbn fails to complete with DCC/netrin-1 interaction.

FIG. 15C: Netrin-1-induced DCC multimerization is inhibited by DCC-5Fbn. Lysates of HEK293T cells transiently transfected with HA-DCC and/or c-myc-DCC expressing constructs with or without netrin-1 (300 ng/mL) and/or DCC-5Fbn (900 ng/mL) were subjected to HA pull-down (IP α-HA), c-myc-DCC presence was revealed with anti-c-myc antibody. Total: Western blot on lysate before pull-down.

Figure 16A:
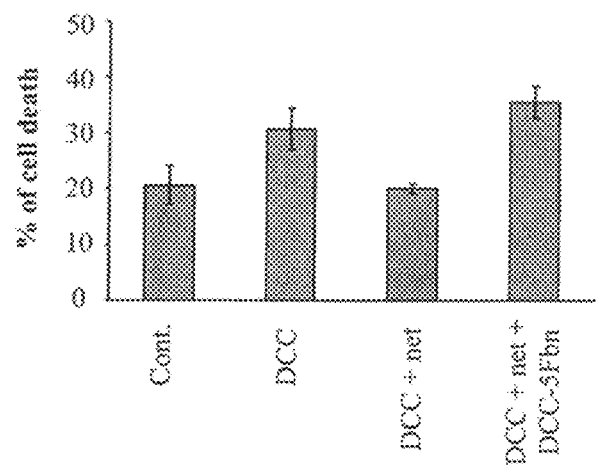
Figure 16B:
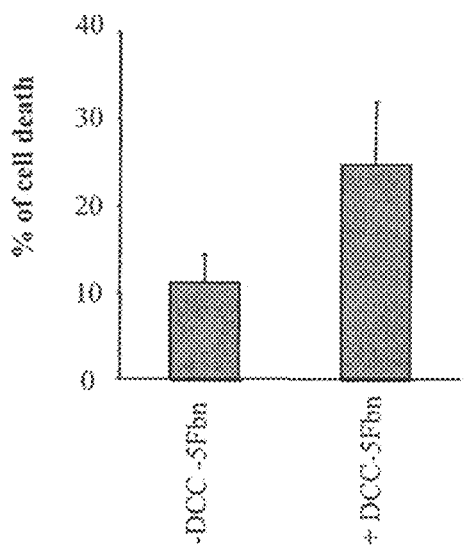

FIGS. 16A and 16B: DCC-5Fbn antagonizes netrin-1-blocking effects on DCC-induced cell death FIG. 16A: HEK293T cells were transiently transfected with a mock (Cont.) or a full length DCC construct and incubated or not with netrin-1 (300 ng/ml) and/or DCC-5Fbn (800 ng/mL). Cell death was assessed by trypan blue staining.

FIG. 16B: Metastatic breast cancer cells 4T1 were cultured in the presence (+DCC-5Fbn) or absence (−DCC-5Fbn) of DCC-5Fbn (300 ng/mL) for 24 hours and cell death was also measured by trypan blue exclusion assay. Standard deviations are indicated (n=23).

EXAMPLE 1

Materials and Methods

Cell Line, Cell Cultures, Transfection Procedure, Reagents and Immunoblots

4T1 and 67NR cells were a kind gift from F. Miller (Detroit, Mich., USA). Cal51, MCF7, MDA-MB231, 453, 361, 157, SK-BR3, CAMA-1, T47D were cultured using standard procedure. Human breast cell lines listed in FIG. 8B and more specifically T47D and SKB7 cell lines were obtained from D. Birnbaun.67NR cells were stably transfected using the lipofectamine reagent (Invitrogen) and puromycine (Sigma) selection. Transient transfections of Human Embryonic Kidney 293T cells (HEK293T) were performed as previously described[10] according to a modified calcium phosphate procedure or using Lipofectamine according to the manufacturer's instructions (Invitrogen). The breast cancer 4T1 cell line was described previously[29], 4T1-luc cells were obtained by stable transfection of a CMV-luciferase vector bearing hygromycine resistance. Clones were selected by luminescence intensity using the luminoskan Ascent Station (Labsystems). Immunoblots were performed as described previously[6] using anti-c-myc (Sigma; 1/200) anti-FlagM2 (Sigma, 1/200) or anti-HA (Sigma; 1/500). The artificial dimerizing agent AP20187 was from Ariad Pharmaceuticals. The complete extracellular domain of DCC (DCC-EC), DCC-EC-Fc were obtained from R&D system and Netrin-1 from Apotech corp. For cell death analysis, caspase activity measurement and immunoprecipitation AP20187 was used at a final concentration of 10 nm and netrin-1 was used as a final concentration of 300 ng/mL.

Human Breast Tumors Samples 51 human breast cancer samples were provided by the tumor bank of the Centre Léon Bérard. Fresh tissue of the tumor was obtained during breast surgery prior and systemic therapy and snap-frozen in liquid nitrogen.

Site Directed Mutagenesis and Plasmid Constructs

PGNET-1 pCMV and pGNET-1 encoding chick netrin-1 were was previously described[6]. pKk was described[22]. The dominant negative mutants for DCC (pCR-DCC-IC- D1209N) and for UNC5H (pCR-UNC5H2-IC-D412N) have been previously described[6,27,7]. HA-DCC was obtained by introducing a HA tag in the template pCMV-DCC[6] by QuikChange site-directed mutagenesis system (Stratagene) using the following primers:

DCC-HA F:
(SEQ ID NO: 1)
5'-CACAGGCTCAGCCTTTTATCCATATGATGTACCGGATTATGCATA

ACATGTATTTCTGAATG-3';

DCC-HA R:
(SEQ ID NO: 2)
5'-CATTCAGAAATACATGTTATGCATAATCCGGTACATCATATGGATAA

AAGGCTGAGCCTGTG-3'.

c-myc-DCC was also obtained by introducing a c-myc tag in the template pCMV-DCC by QuikChange using the following primers; DCC-myc F: 5'-CACAGGCTCAGCCTTTGAGCAGAAGTTGA-TAAGTGAGGAAGATCTGTAACATG TATTTCT-GAATG-3' (SEQ ID NO:3) DCC-myc R: 5'-CAT-TCAGAAATACATGTTAC AGATCTTCCTCACTTCTCAACTTCTGCT-CAAAGGCTGAGCCTGTG-3' (SEQ ID NO:4).

HA-Fv2E encoding expression vector (in pC4M) from the Argent Regulated Homodimerization kit is from Ariad Pharmaceuticals. From this plasmid, the HA-Fv2E-DCC-EC plasmid was constructed. A PCR fragment of the intracellular domain of DCC (1122-1447) was obtained with the primers: F 5'-TATGTCGACCGACGCTCTTCAGCCCAGCAGAGA-3' (SEQ ID NO:5) and R 5'-TATGAATTCT-TAGTCGAGTGCGTAGTCTGGTACGTCGTACGGA-TAAAAGGCTGA GCCTGTGATGGCATTAAG-3' (SEQ ID NO:6).

The reverse printer fused to the HA tag to C-terminal end of DCC. The PCR fragment was subcloned in HA-Fv2E by SalI and EcoRI restriction digestion. The c-myc-Fb2E-DCC-IC was obtained using the QuikChange site-directed mutagenesis system (Stratagen) with pC4M-Fv2E-DCC-IC-HA as template and the following primers: primer F: 5'-CT-TAATGCCATCACAGGCTCAGCCTTT-GAACAGAAACTCATCTCTGAAGAGGAT CTGTAAGAATTCATAAAGGGCAAT-3' (SEQ ID NO:7) and primer R: 5'ATTGCCCTTTATGAATTCTTACA-GATCCTCTTCAGAGATGAGTTTCTGTTCAAG GCT-GAGCCTGTGATGGCATTAAG-3' (SEQ ID NO:8).

HA-UNC5G2 (in pcDNA3.1) has already been described[7] the constructs encoding FlagM2-UNC5H2 was generated by cloning in p3×Flag-CMVTM-7.1 (Sigma) the NotI-EcoI PCR fragment derived from HA-UNC5H2 as template and the following primers: primer F 5'-GCGCGGCCGCAGGGCCCGGAGCGGG-3' (SEQ ID NO:9) and primer R 5'-CGGAATTCTCAGCAATCGC-CATCAGTGGTC-3' (SEQ ID NO:10).

HA-Fv2E-UNC5H2-IC- and c-myc-Fv2E-UNC5H2-IC in pC4M were generated by PCR amplification of the UNC5H2 intracellular domain using the following primers: UNC5H2-HA F 5'-CGGTCGACGTGTACCG-GAGAAACTGC-3' (SEQ ID NO:11) and UNC5H2-HA R 5'-GCGAATTCTCATGCATAATCCGGCACATCATACG-GATAGC AATCGCCATCAGTGGTC-3' (SEQ ID NO:12), and UNC5H2-myc R5'-GCGAATTCTCTCACA-GATCCTCTTCTGAGATGAGTTTTTGTTCGCAATCGC-CATCA GTGGTC-3' (SEQ ID NO:14) respectively. The PCR fragments were cloned in HA-Fv2E by SalI and EcoRI restriction digestion.

The cDNA encoding the HA-Fv2E-UNC5H2-IC and c-myc-Fv2E-UNC5H2-IC fusion proteins were then subcloned in pcDNA3.1-TOPO by PCR using the following primers: Fv2E F 5'-CCACCATGGGGAGTAGCA-3' (SEQ ID NO:15) and UNC5H2-HA R 5'-TCATGCAT-AATCCGGCACATCATACGGATAGCAATCGC-CATCAGTGGTC-3' (SEQ ID NO:16), and Fv2E 5'-CCAC-CATGGGGAGTAGCA-3' (SEQ ID NO:15) and UNC5H2-myc R 5'-TCACAGATCCTCTTCTGAGAT-GAGTTTTTGTTCGCAATC GCCATCAGTGGTC-3' (SEQ ID NO:17) respectively and HA-Fv2E-UNC5H2-IC and c-myc-Fv2E-UNC5H2-IC in pC4M as respective templates.

Ps974-DCC-5Fbn allowing bacterial expression of the fifth fibronectin type III domain of DCC was obtained by inserting a PstI/BamHI DNA fragment generated by PCR using pDCC-CMV-S as a template.

DCC-5Fbn production:

DCC-5Fbn production was performed using a standard procedure. Briefly, BL21 cells were forced to express DCC-5Fbn in response to imidazole and the BL21 lysate was subjected to affinity chromatography using Flag-agarose (Sigma).

Immunoprecipitation:

Coimmunoprecipitations were carried out on HEK293T cells transfected with various tagged constructs as described previously[27] Briefly, HEK293T cells were lysed in 50 mM HEPES pH 7.6, 125 mM NaCl, 5 mM EDTA and 0.1% NP-40 in the presence of protease inhibitor, and further incubated with anti-HA (Sigma), anti-c-myc antibody (Sigma), anti-FlagM2 (Sigma) and protein-A Sepharose (Sigma). Washes were done in 50 mM HEPES pH 6.6, 125 mM NaCl, 5 mM EDTA.

Binding Assay and ELISA Competition Assay:

DCC-5Fbn (100 ng) or IL3-R (R&D systems, 600 ng) was coated on maxisorp plate (Nunc) and increasing doses of netrin-1 (Apotech) were added (0 to 800 ng) for binding assay. DCC-EC (R&D systems, 125 ng) was coated on maxisorp plate for ELISA competition assay. Netrin-1-Flag M2 (50 ng) and competitor DCC-EC (125 ng) or DCC-5Fbn (625 ng) were then added simultaneously. After washes, for both binding assay or ELISA competition assay, residual netrin-1-FlagM2 still fixed was revealed with an anti-FlagM2 antibody (Sigma).

DCC/Netrin-1 ELISA assays:

DCC-EC-Fc (1.25 ng/ml) or UNC5H2-EC-Fc (0.5 ng/ml) was adsorbed on 96-well maxisorp plate (Nunc) according to manufacturer instruction. Flag-tagged Netrin-1 (0.5 ng/ml) was then added together with increased concentrations of DCC-EC-Fc. After a 1 hour incubation, plates were extensively washed and bound netrin-1 was detected by immunolabelling using an anti-flagM2 antibody (Sigma) and a HRP-goat-anti-mouse (Jackson). Colorimetric measurement was performed on the multilabel Victor station (Wallac).

Cell Death Assays:

67NR, 4T1, CAL51, T47D and SKBR7 were grown in serum-poor medium and were treated (or not) with DCC-EC-Fc or DCC-5Fbn for 24 hours. Cell death was analyzed using trypan blue staining procedures as described previously[6]. The extent of cell death is presented as the percentage of trypan blue-positive cells in the different cell populations. To select transfected cells, cells were co-transfected with the surface marker pKk and the plasmid encoding genes of interest. Transfected cells expressing the marker were magnetically labeled with MA Select Microbeads and separate using a MCS Separator and Separation Columns (Miltenyi Biotec). Trypan blue exclusion was assayed on these purified cells. Cell survival was also measured by MTT assay using Vybrant MTT assay kit (Molecular Probes) according to the manufacturer procedures.

Caspase Activity Measurement:

Relative Caspase activity was determined by flow cytometric analysis as follows: $2 \cdot 10^5$ treated cells were harvested, washed once in 1 ml PBS, and resuspended in 200 μl staining solution containing FITC-VAD-fmk (CaspACE, Promega). After incubation for 60 min at 37° C., cells were washed in 1 ml PBS and resuspended in 200 μl PBS for flow cytometry analysis. Stained cells were counted using a FACS Calibur (Becton Dickinson) and CellQuest analysis software with excitation and emission settings of 488 nm and 515-550 nm (filter FL1), respectively. Caspase-3 activity was measured by using the Caspase-3 assay from BioVision. Caspase activity is presented as the ratio between the caspase activity of the sample and that measured in HEK293T cells transfected with pCMV. For cell death analysis and caspase activity measurement, AP20187 or/and netrin-1 or/and DCC-5Fbn were added in cell culture medium 20 hours and 1 hour before collecting cells.

Qualitative RT-PCR:

To assay netrin-1 expression in human breast tumors, total RNA was extracted from biopsies of patients undergoing surgery for breast cancer using Nucleopspin RNAII kit (Macherey-Nagel) and 1 μg was reverse-transcribed using the iScript cDNA Synthesis kit (BioRad). Real-time quantitative RT-PCR was performed on a Light Cycler 2.0 apparatus (Roche) using the Light Cycler FastStart DNA Master SYBERGreen I kit (Roche). Reaction conditions for all optimal amplification, as well as primer selection of netrin-1, were determined as already described[18]. The ubiquitously expressed human PBGD, TBP and mouse RPLP0 genes showing the less variability in expression between normal and breast tumoral tissues[25,28] were used as internal controls. The following primers were used:

```
PBGD:
                                   (SEQ ID NO: 18)
FOR:    5'-CTGGAGTTCAGGAGTATTCGGGG-3', (SEQ ID NO: 19)
REV:    5'-CAGATCCAAGATGTCCTGGTCCTT-3';

TBP:
                                   (SEQ ID NO: 20)
FOR:    5'-CACGAACCACGGCACTGATT-3', (SEQ ID NO: 21)
REV:    5' TTTTCTTGCTGCCAGTCTGGAC 3';

Human netrin-1-NTN1:
                                   (SEQ ID NO: 22)
FOR:    5'-TGCAAGAAGGACTATGCCGTC-3', (SEQ ID NO: 23)
REV:    5'-GCTCGTGCCCTGCTTATACAC-3';

UNC5B:
                                   (SEQ ID NO: 24)
FOR:    5'-TGCAGGAGAACCTCATGGTC-3', (SEQ ID NO: 25)
REV:    5'-GGGCTGGAGGATTACTGGTG-3';

DCC:
                                   (SEQ ID NO: 26)
FOR:    5'-AGCCAATGGGAAAATTACTGCTTAC-3', (SEQ ID NO: 27)
REV:    5'-AGGTTGAGATCCATGATTTGATGACG-3';

UNC5C:
                                   (SEQ ID NO: 28)
FOR:    5'-GCAAATTGCTGGCTAAATATCAGGAA-3', (SEQ ID NO: 29)
REV:    5'-GCTCCACTGTGTTCAGGCTAAATCTT-3'.
```

Mice, Intravenous and Mammary Gland Injections, Measurement of Metastasis Development:

Syngenic mice model. Female BALB/cBYJ mice of 8-11 weeks of age from Jackson Laboratory were used for surgery. For mammary gland injection of 67NR cells, mice were anesthetized with 2,2,2-tribromomoethanol and $10^6$ cells in 50 μl PBS were injected into the mammary gland and mice were sacrificed when the tumor exceeded 1.5 cm and caused impediment to the movement of the animal. For intravenous injection, $10^5$ tumor 4T1-luc cells in 150 μl PBS were injected into a tail vein and mice were either sacrificed at day 13-15 (after 4T1 cells injection) or at day 20-23 (after 67NR cells injection) or analyzed using luminescence recording. When animals were sacrificed, lungs were removed, weighed and compared to the whole weight of the animal, and metastatic nodules counted.

Xenograft in Nude Mice

Five-week-old (20-22 g body weight) female athymic nu/nu mice were obtained from Charles River. The mice were housed in sterilized filter-topped cages and maintained in a pathogen-free animal facility. Human breast cancer cell lines (SKBR7, T47D and H358) were implanted by s.c. injection of $5 \cdot 10^6$ cells in 200 μL of PBS into the left flank of the mice. When tumors were established (5 weeks for T47D, 2 weeks for SKBR7 and 5 days for H358, PBS or 20 μg of DCC-5Fbn were administered into the tumor (i.t.) everyday during 14 days. Tumor sizes were measured by a caliper. The tumor volume was calculated with the formula $v=0.5*(length*width^2)$.

Tumor Analysis:

4 μm-thick lung sections were prepared and stained with hematoxylin-eosin-saffron. Histological classification and grading of neoplastic lesions was performed in a blinded fashion and according to standard procedures. For in vivo imaging of metastasis using 4T1-luc cells, the light resulting from the bioluminescent oxidation of the intra-peritoneally injected endotoxin-free luciferin (Promega) (120 mg/kg bodyweight) was detected and quantified (10 minutes after injection) with a NightOWL LB 981 NC 100 system from Berthold Technologies, using an anaesthesia system with gaseous isoflurane from TEM SEGA.

EXAMPLE 2

Netrin-1 Dictates Metastasis of Breast Tumor by Inhibiting Apoptosis

We first analysed netrin-1 and its dependence receptors—i.e., DCC and UNC5H expression by Q-RT-PCR in a panel of 30 breast primary tumors, 15 of which were without known metastatic evolution, and 15 that were metastatic at diagnosis. While DCC was barely detectable and UNC5H failed to show significant change between the two types of tumors, netrin-1 appeared to be significantly more expressed in metastatic breast tumors than in non-metallic breast tumors (FIG. 1A).

60% of tested metastatic breast tumors showed an overexpression of netrin-1 (range from 1.4 from 9.6 fold, p<0.015) (Table 1).

TABLE 1

The percentage of samples showing a netrin-1 expression higher than the average expression in non-metastatic biopsies is indicated, as is the range of the over-expression.

| n = 15 | metastasis | non metastasis |
| --- | --- | --- |
| % of breast tumors that over-express netrin-1 | 60 | 33 |
| Range of over-expression of netrin-1 | 1.4-9.6 | 1.6-2.9 |

In mice, Miller and colleagues developed a powerful model to study the biology of metastatic versus non-metastatic tumors: from a single primary mammary tumor that occurred naturally n a BALB/c mouse, a series of cell lines were obtained that showed different metastatic potentials when injected into syngenic mice. In particular, while 67NR cells from primary mammary tumors but no metastasis, 4T1 cells form primary tumors and metastasis, especially in the lung, the bone marrow and the liver[20]. Interestingly, while netrin-1 failed to be detected in 67NR cells, netrin-1 was highly expressed in 4T1 cells (FIG. 1B).

To assay whether the metastatic potential of 4T1 cells, compared to that of 67NR cells, was related to netrin-1 expression, 67NR cells were forced to stably express netrin-1. Mock transfected 67NR cells or 67NR-net cells that express netrin-1 (FIGS. 2A, 2B) were injected in mammary gland or i.v. and metastasis was monitored by anatomy-pathology examination of lungs. Both cell lines failed to form metastasis when injected in fat pad, suggesting that the presence of netrin-1 in 67NR is not sufficient to allow lung metastasis formation from the primary site. However, when cells were injected i.v., a significant increase of metastasis in the lungs was detected in the netrin-1 expressing 67NR (FIG. 2C).

See Table 2 showing the number of under-pleural (metastasis outside the lung) and intra-parenchymatous nodules (metastasis in the lung).

TABLE 2

| | under-pleural lesions | | Intra parenchymatous Lesions (lung metastasis) | |
| --- | --- | --- | --- | --- |
| mice injected with clone: | Number of lung Affected | Number of noduled per lung (range) | Number of lung affected | Number of nodules per lung (range) |
| 67ZNR1 | 3 | 0-5 | 0 | 0 |
| 67NR2 | 2 | 0-2 | 0 | 0 |
| 67NR-net1 | 3 | 0-5 | 1 | 0-4 |
| 67NR-net2 | 1 | 0-3 | 2 | 1-2 |

Thus, netrin-1 expression appears to be a crucial event that supports metastasis formation, probably by favoring tumor cells after intrathion.

Because netrin-1 appears to be sufficient for the metastatic potential of 67NR cells after intravation and because netrin-1 was shown to inhibit netrin-1 dependence receptors-induced cell death[6, 7, 18], we next investigated whether autocrine production of netrin-1 provides a selective advantage to 4 T1 cells by inhibiting DCC/UNC5H-induced cell death in these cells. A domain located in the N-terminus of netrin-1 (the so-called laminin-V1 domain) interacts with both DCC and UNC5H receptors (FIG. 3A;[21]), so that a soluble extracellular domain of DCC (DCC-EC-Fc) can inhibit both DCC/netrin-1 and UNC5H/netrin-1 interaction (not shown). DCC-EC-Fc was then added to a culture of 4T1 cells and cell death was monitored either by a trypan blue exclusion assay (FIG. 3B) or by measuring caspase activity (FIG. 3C). As shown in FIG. 3C, addition of the completing protein in the culture medium triggers death of 4T1 cells in a dose-dependent manner. Moreover, this effect is specific, as DCC-EC-Fc had no effect on 67NR cell death and IL3R-EC-Cc (the extracellular domain of IL3 receptor) failed to trigger 4T1 cell death (FIGS. 3B, 3C). This effect is due to netrin-1 inhibition, as addition of an excess amount of netrin-1, together with DCC-EC-Fc inhibited the pro-apoptotic activity of DCC-EC-Fc on 4T1 cells (not shown). To restrict the competition to a smaller domain, we produced the fifth fibronectin type III domain of DCC, which is known to interact with netrin-1[21]. Addition of this domain—DCC-5Fbn—had a similar pro-apoptotic activity on 4T1 cells (FIG. 3D). Thus, while netrin-1 appears to confer metastatic potential to tumor cells in mice, these netrin-1 expressing metastatic tumor cells can be engaged toward apoptosis by inhibition of the netrin-1/receptors interaction.

To further analyze whether this holds true in human breast tumor cells, netrin-1 expression was analysed in a panel of human metastatic breast cancer cell lines (see Table 3).

TABLE 3

| Human breast carcinoma cell line | Netrin-1 transcriptional expression | DCC-EC-Fe sensitivity |
| --- | --- | --- |
| MRA-MB 157 | ++++ | +/- |
| MGF-7 | ++++ | - |
| CAMA-1 | +++ | - |
| SKBR3 | ++ | ND |
| SAV-NUDE | ++ | ND |
| Cal51 | ++ | +++ |
| MDA-MB231 | + | ++ |
| MDA-MB453 | + | + |
| T47D | - | ND |
| T47D* | ++ | ++ |

*Carried out on another T47D cell line

Table 3 showing the different human metastatic breast cell lines analysed for the netrin-1 expression by Q-RT PCR as in FIGS. 1A, 1B, and their sensitivity to DCC-EC-Fc by measurement of cell death by trypan blue exclusion. The relative amount of netrin-1 expression and DCC-EC-Fc sensitivity are indicated by (+), while the absence of these criteria is indicated by (−). In some cell lines the DCC-EC-Fc has not been determined (ND).

As expected, netrin-1 is expressed in a large number of metastastic cell lines and some of them undergo apoptosis when cultured in the presence of DCC-EC-Fc. As an example, CAL51 cells underwent apoptosis in a dose-dependent manner in response to DCC-EC-Fc. As above, addition of netrin-1 in excess reverts the effect of DCC-EC-Fc, supporting the view that the competing proteins kill these human cell lines by inhibiting the netrin-1/netrin-1 receptors interaction. Moreover, a clonal selection from CAL51 cells allowed the establishment of a CAL51-36 cell line, that tis much more susceptible to cell death in response to DCC-EC-Fc (FIG. 4B). Because the DCC-EC-Fc or DCC-5Fbn may consequently represent good tools to trigger selective apoptosis of human metastatic tumors cells.

Here we shown that netrin-1 expression may be considered as a marker of breast tumor dissemination. More than half of the breast tumors with metastasis propensity showed elevated netrin-1 expression. Both the mice model described above and the data obtained on human breast cancer cell lines support the view that this elevated netrin-1 level is a selective advantage acquired by the cancer cell to escape netrin-1-dependence receptors induced apoptosis and, consequently, to survive independently of netrin-1 availability. From a mechanistic point of view, this autocrine expression of netrin-1 inhibits cell death induced by UNC5H. Indeed, DCC was barley detectable in the two groups—metastastic and non metastatic—of breast cancers studied, hence suggesting that DCC is either down-regulated early during breast tumorigenesis or is only weakly expressed in breast tissue. Moreover, inhibition of UNC5H-induced apoptosis by co-expression of a dominant negative mutant form of the UNC5H pro-apoptosis by co-expression of a dominant negative mutant form of the UNC5H prop-apoptosis by co-expression of a dominant negative mutant form of the UNC5H pro-apoptotic activity inhibits CAL51 cell death in response to DCC-EC-Fc (not shown). This may fit with the recent observation that part of UNC5H2 pro-apoptotic activity passes through the activation of the serine/threonine DAPK[22] a protein involved in metastasis regulation[23].

These observations not only provide evidence for the importance of the ligand/dependence receptor pair in the regulation of tumor development, but also enlighten a new therapeutic strategy. Indeed, as of today, there is no efficient treatment for patients with metastatic breast cancer, a lack of treatment that leads to the death of 400,000 women worldwide per year[24]. Here we propose that a treatment based on inhibition of the interaction between netrin-1 and its dependence receptors could positively affect half of the patients suffering from metastatic breast cancer. These treatments could include chemical drugs, monoclonal antibodies or the DCC-5Fbn protein presented here. Whether this should be considered as a strategy preventing metastasis formation, which would imply a long-term preventive treatment on women diagnosed with primary breast cancer, or as a strategy that could be used to induce metastasis regression remains to be shown. Future clinical trials should also answer this point.

Here we describe that, unlike human non-metastatic breast tumors, the majority of metastatic breast cancers shows and over-expression of netrin-1. In a mice model, we demonstrate that in non-metastatic mammary tumor cells, forced expression of netrin-1 is associated with metastasis in the lungs. Moreover, mice or human metastatic tumor cell lines, that were shown to highly express netrin-1, undergo apoptosis when the netrin-1/receptors interaction is inhibited by a competing protein. Thus, netrin-1 is a marker for human metastatic cancer such as metastatic breast and inhibition of the netrin-1/receptors interaction represents a therapeutic approach to induce metastatic cell death.

EXAMPLE 3

Restoration of the Netrin-1 Dependence Receptors Pathway Triggers Apoptosis in Metastatic Breast Tumors Netrin-1 and its dependence receptors—i.e., DCC, UNC5H2, UNC5H3 expression were analysed by Q-RT-PCR in a panel of 51 breast tumors. It includes patients whose tumors were either localized to the breast (N0, 16 patients), had nodal involvement (N+, 19 patients) or had distant metastatic disease at the time of diagnosis (M+, 16 patients). While DCC was barley detectable and UNC5H expression failed to display significant changes between the different types of tumors (not shown), netrin-1 is significantly more expressed in N+ tumors than in N0 tumors (median: 1.8 versus 0.5, p=0.007) with a range of netrin-1 expression higher in N+ tumors (FIG. 5 and Table 4).

TABLE 4

The percentage of samples showing a netrin-1 expression higher than the average expression in N0 biopsies, 5 fold higher or 15 fold higher is indicated, as is the range of the over-expression.

| | | n = 51 | | |
|---|---|---|---|---|
| | | N0 Localised to breast (n = 16) | N+ Nodal involvement (n = 19) | M+ Distant metastasis (n = 16) |
| % of breast tumors that over-express netrin-1 | | 31 | 73.7 | 93.7 |
| % of breast tumors that over-express netrin-1 | More than 5 fold | 0 | 31.5 | 62.5 |
| | More that 15 fold | 0 | 0 | 37.5 |
| Range of over-expression of Netrin-1 | | 0.02-4.6 | 0.03-12.8 | 0.6-111.7 |

31.5% of the N+ tumors show at least a 5 fold increase in netrin-1 expression while no such increase was detected in any tested N0 tumors (FIG. 4 and Table 4). An even more striking difference is observed when comparing netrin-1 expression in M+ versus N0 tumors (median: 7.8 versus 0.5, p<0.0001). Along this line 62.5% of M+ tumors show at least a 5 fold increase in netrin-1 expression. A significant difference in netrin-1 expression also exists between N+ and M+ tumors (median: 1.8 versus 7.8, p=0.009). Moreover netrin-1 overexpression is higher in M+ tumors than in N+ tumors, as 37.5% of M+ tumors display more than a 15 fold increase in netrin-1 level, while such an increase is not detected in N+ tumors (FIG. 5 and Table 4). Thus, netrin-1 up-regulation is a marker of nodal involvement and distant metastatic disease in human breast cancer.

In mice, Miller and colleagues developed a powerful model to study the biology of metastatic versus non-metastatic tumors: from a single primary mammary tumor that occurred naturally in a BALB/c mouse, a series of cell lines were obtained that showed different metastatic potentials when injected into syngenic mice. In particular, while 67NR cells form primary mammary tumors but no metastasis, 4T1 cells form primary tumors and metastasis, especially in the lung, the liver and the bone marrow[20]. Interestingly, while netrin-1 failed to be detected in 67NR cells, netrin-1 was highly expressed in 4T1 cells (FIG. 1B).

To first assay whether the metastatic potential of 4T1 cells, compared to that of 67NR cells, was related to netrin-1 expression, 67NR cells were forced to stably express netrin-1. Mock transfected 67NR cells or 67NR cells that express netrin-1 (FIGS. 2A and 2B) were injected into mammary glands and metastasis was monitored by anatomo-pathological examination. Both cell lines failed to efficiently form metastasis in liver or in lungs when injected in mice fat pads (19 mice were injected with netrin-1 expressing 67NR cells and only two suspicions of micro-metastases, one in the lung and one in the liver were detected) (Table 5).

TABLE 5

Lungs and liver metastasis of fat pad-injected 67NR versus netrin-1 expressing cells. One control cell clone bearing puromycine resistance (67NR-mock), one netrin-1 expressing cell clone (67NRnet1) and one polyclonal population of netrin-1 stably transfected 67NR (67NR-net1-polyclonal) were injected in fat pad of mice and metastasis was analysed in the lung or liver environment.

| Cells injected | Mice (n) | Primary tumors | Metastasis | Comment |
|---|---|---|---|---|
| 67NR-mock | 9 | 9 | 0 | |
| 67NR-net1 | 7 | 7 | 0 | Suspicion of 1 micrometastase in liver |
| 67NR-net1 polyclonal | 12 | 12 | 0 | Suspicion of 1 micrometastase in lung |

Thus, netrin-1 expression in tumor cells is not sufficient to enable metastasis formation from the primary site.

Because netrin-1 was shown to inhibit netrin-1 dependence receptors-induced cell death[6, 7, 18], we next investigated whether the autocrine production of netrin-1 detected in metastatic 4T1 cells confers a selective advantage to these cells, by inhibiting DCC/UNC5H-induced cell death. To assay this, we looked for a compound that may titrate netrin-1. It was reported that a domain located in the N-terminus of netrin-1 (the so-called laminin-VI domain) interacts with both DCC and UNC5H receptors (FIG. 3A;[21]). We show that a soluble extracellular domain of DCC (DCC-EC-Fc) can inhibit both DCC/netrin-1 and UNC5H2/netrin-1 interaction, as measured by ELISA assay (FIG. 6A). DCC-EC-Fc was then added to a culture of 4T1 cells and cell death was monitored, either by a trypan blue exclusion assay (FIGS. 3B and 6B) or by measuring caspase activity by flow cytometry (FIGS. 3C and 6C). As shown in FIGS. 3B, 3C, 6B and 6C addition of the competing protein in the culture medium triggers death of 4T1 cells in a dose-dependent manner. This effect is specific, as DCC-EC-Fc had no effect on 67NR cell death (FIGS. 3B, 3C, 6B and 6C) and IL3R-EC-Cc (the extracellular domain of the IL3 receptor) failed to trigger 4T1 cell death (FIG. 3D). Thus, 4 T1 cells survive through autocrine production of netrin-1, which blocks netrin-1 receptors-induced cell death.

Because the complete extracellular domain of DCC appear as only of modest interest for use in vivo and in therapy (DCC-EC-Fc is about 1100 amino-acid large), we looked for an alternative polypeptide from the DCC extracellular domain, which could trigger apoptosis in 4 T1 cells. We consequently produced the fifth fibronectin type III domain of DCC, DCC-5Fbn, which is known to interact with netrin-1[21] (FIG. 3A). Interestingly, this 100 amino-acid protein does not interfere with the binding of DCC/netrin-1 or UNC5H/netrin-1, but affects the ability of netrin-1 to trigger multimerization of these receptors (see Example 4). As DCC and UNC5H multimerization is a pre-requisite for the netrin-1 inhibitory activity on DCC/UNC5H-induced cell death, the addition of DCC-5Fbn triggers apoptosis in DCC-expressing cells cultured in the presence of netrin-1[22] and triggers death of both 4T1 (FIG. 7A).

We next instigated whether the cell death effect observed in vitro may be extended in vivo. To do so, 4T1 cells were stably transfected with a luciferase-based vector and 4T1-luc cells were intravenously (i.v.) injected into syngenic BALB/c mice. Mice were then intraperitonealy (i.p.) and i.v. injected (1 injection every two days, once i.v., once i.p.) from day 0 to day 13 with wither PBS buffer or Flag-tagged-DCC-5Fbn (1.25 μg/mouse g/injection). Metastasis formation was then analyzed using luminescence recording. As shown in FIGS. 7B and 7C, when i.v. injected, 4T1-luc cells efficiently colonize lungs. On the opposite, mice treated with DCC-5Fbn shown a dramatic reduction of lung metastasis (FIGS. 7B and 7C). This inhibition of metastasis formation was then confirmed by anatomo-pathological examination of lungs, (not shown, see Table 6).

TABLE 6

Total number of lung metastatic nodules in individual mice were counted under a dissection scope in the two treated populations (+PBS, +DCC-5Fbn)

| Treatment | Mice (n) | Average of Metastatic per mouse | Range of metastasis per mouse |
|---|---|---|---|
| PBS | 10 | 42.4 | 0-75 |
| DCC-5Fbn | 10 | 2.6 | 0-6 |

Similar results were obtained when we performed daily i.p. injection of GST-tagged-DCC-5Fbn instead of Flag-tagged-DCC-5Fbn and GST-FADD instead of PBS (not shown). Thus, in mice, the inhibition by DC-5Fbn of the pro-survival activity conferred by netrin-1 autocrine expression is associated with metastasis prevention.

The acquire survival advantage through netrin-1 autocrine expression is not restricted to murine tumor cells, as it is detected in human breast cancer cell lines. Indeed, netrin-1 was shown to be expressed in a sizeable fraction of human breast cancer lines (FIG. 8A) and addition of DCC-EC-Fc or DCC-5Fbn to naturally netrin-1 expressing human breast adenocarcinoma T47D or SKBR7 cell cultures triggers cell death induction measured either by caspase-3 activity assay or MTT assay (FIG. 8B) and not shown). This effect is due to netrin-1 inhibition, as addition of an excess amount of netrin-1, inhibited the pro-apoptotic activity of DCC-EC-Fc/DCC-5Fbn (not shown). To monitor the anti-tumor effect of DCC-5Fbn, xenografts of T47D cells were implanted in nude mice. When tumors reached a palpable size, mice were daily treated with either PBS or DCC-5Fbn and tumor volume was determined for 18 days. Similarly to the data obtained in the syngeneic model above, DCC-5Fbn fully inhibits tumor growth (Table 7).

TABLE 7 showing the number and behavior of xenografted T47D tumors have been treated either with PBS or DCC-5Fbn. The number of tumors that has grown in size more than 40% and the number of tumors that has a reduced size (more than 30%) are indicated

| Treatment | Number of mice | Tumor growth (>40%) | Tumor regression (>30%) |
|---|---|---|---|
| PBS | 4 | 3 | 0 |
| DCC-5Fbn | 5 | 0 | 3 |

Here we show that netrin-1 expression may be considered as a marker of breast tumor ability to disseminate. Most of the breast tumors with metastasis propensity showed elevated netrin-1 expression. Both the data obtained on human/mice breast cancer cell line and the syngeic/human xenograft mice models described above and support the view that this elevated netrin-1 level is a selective advantage acquired by the cancer cell to escape netrin-1-dependence receptors induced apoptosis and, consequently, to survive independently of netrin-1 availability. From a mechanistic point of view, in the human pathology, this autocrine expression of netrin-1 probably inhibits UNC5H-induced cell death. Indeed, DCC was barely detectable in the different groups (N0, N+, M+) of breast cancers studied, hence suggesting that DCC is either down-regulated early during breast tumorigenesis or is only weakly expressed in breast tissue. Moreover, inhibition of UNC5H inducted apoptosis by co-expression of a dominant negative mutant form of the UNC5H pro-apoptotic activity inhibits human breast cancer cell death in response to DCC-EC-Fc (not shown).

Thus, as predicted by the dependence receptor model, we have now shown that a tumor cell can escape dependence receptor dependency in at least three manners. First, expression of the dependence receptor can be down-regulated, as extensively described for DCC and more recently for UNC5H[15, 17, 19, 29]. Second, the downstream death signaling can be shut down. Along this line, we have recently shown that UNC5H2 pro-apoptotic activity relies on the binding of UNC5H2 to the serine/threonine DAPK[22], a protein that was demonstrated to be involved in metastasis regulation and down-regulated in human malignancy[21]. Similarly, a recent report by Stupack and colleagues shows that, in the case of some integrins that act as dependence receptors, caspase-8, which triggers the cell death mediated by these integrins, is crucial for neuroblastoma metastasis[30]. Here we show that a third selective advantage for the tumor cell is the self-production of the dependency ligand. One intriguing question remains as to why breast tumors with metastatic propensity seem to have preferably selected netrin-1 self-production rather than receptor loss, while colorectal tumors have mostly selected loss of the receptors rather than gain of netrin-1 expression—indeed, only 7% of colorectal cancers show an increase of netrin-1 expression[18]. A possible explanation is that netrin-1 expression not only confers a gain in survival to the migrating cells, but also possibly a gain in the non-apoptotic/positive signalling of netrin-1 receptors. Along this line, it is important to note that netrin-1 was originally described as a guidance cue[31], which, even though completely unproven, could play a role in the tropism of metastatic cells. Other proposed roles of netrin-1 include adhesion and morphogenesis regulation[32-34], both mechanisms that may be of importance for metastasis development. Similarly, netrin-1 was recently proposed to play a role during embryonic angiogenesis and as an angiogenic factor that somehow could favor metastasis development even though conflicting results have been published[26-38], we cannot at this stage discard the role of netrin-1 as an angiogenic factor that somehow could favor metastasis development at the secondary site. However, the gain of "positive" signalling by netrin-1 autocrine expression is probably not sufficient per se to promote metastasis, as forced expression of netrin-1 in non-metastatic cells failed to be associated with metastasis formation.

These observations not only provide evidence for the importance of ligand/dependence receptors pairs in the regulation of tumor development, but also enlighten a new therapeutic strategy. Indeed, as of today, there is no efficient treatment for patients with metastatic breast cancer, a lack of treatment that leads to the death of 400,000 women worldwide per year[24]. Here we propose that a treatment based on inhibition of the interaction between netrin-1 and its dependence receptors could positively affect a large fractions of the patients suffering from metastatic cancer, such as breast cancer—i.e. patients who would shown high netrin-1 expression in primary tumors—. These treatments could include chemical drugs, monoclonal antibodies or the DCC-5Fbn protein presented here.

EXAMPLE 4

Netrin-1 Expression and Inhibition of Netrin-1 Activity in Other Human Tumors

A) Netrin-1 is a marker of aggressiveness in human neuroblastoma (see FIG. 9A, its legend and table 8) and inhibiting netrin-1 activity promotes neuroblastoma cell death (see FIG. 10B ant its legend).

TABLE 8

26 neuroblastoma cell lines (either obtained directly from patient tumors at Centre Léon Bérard (CLB-X) or classic neuroblastoma cell lines (IMR32, SHEP, SHSY or SKNAS)) were tested as in (a) for netrin-1 expression by Q-RT-PCR. Netrin-1 level is indicated as (−) no netrin-1, (+, ++, +++) low to high netrin-1 level. It can be noted that a significant fraction of cell lines have high expression of netrin-1.

| Cell line | netrin-1 |
|---|---|
| CLB-BAB | − |
| CLB-BAC | − |
| CLB-BAR | − |
| CLB-BARREC | − |
| CLB-BEL | + |
| CLB-BOULT | ++ |
| CLB-BER2 | − |
| CLB-BERLUD | − |
| CLB-CAR | − |
| CLB-ESP | −/+ |
| CLB-GAR | − |
| CLB-GHE MO | − |
| CLB-GHE PCT | − |
| CLB-HUT | +++ |
| CLB-MAR MO | −/+ |
| CLB-MAR LT | + |
| CLB-PEC | − |
| CLB-REM | +++ |
| CLB-SED | + |
| CLB-TRA | − |
| CLB-VOL | ++++ |
| IGRN91 | −/+ |
| IMR32 | +++ |
| SHEP | −/+ |
| SHSY 5Y | −/+ |
| SKNAS | ++++ |

B) Netrin-1 is overexpressed in a large fraction of glioma (see FIG. 10A and its legend) and inhibition of netrin-1 activity promotes glioma cell death (see FIG. 10B and its legend).

C) Netrin-1 is overexpressed in human lung cancer (see FIG. 11A, its legend and table 9) and inhibition of netrin-1 activity promotes lung cancer cell death and prevents lung cancer development (see FIGS. 12C and 12D and their legends).

TABLE 9

Lung cancer cell lines either derived from small-cell-lung cancer (SCLC) or non-small-cell-lung cancer (NSCLC) were tested as in (a) for netrin-1 expression by Q-RT-PCR. Netrin-1 level is indicated as (−) no netrin-1, (+, ++) low to high netrin-1 level. It can be noted that a significant fraction of cell lines have high expression of netrin-1.

| Cell line | netrin-1 |
|---|---|
| NSCLC | |
| A549 | + |
| H322 | ++ |
| H358 | ++ |

TABLE 9-continued

Lung cancer cell lines either derived from small-cell-lung cancer (SCLC) or non-small-cell-lung cancer (NSCLC) were tested as in (a) for netrin-1 expression by Q-RT-PCR. Netrin-1 level is indicated as (−) no netrin-1, (+, ++) low to high netrin-1 level. It can be noted that a significant fraction of cell lines have high expression of netrin-1.

| Cell line | netrin-1 |
|---|---|
| H460 | − |
| H1299 | + |
| SCLC | |
| H69 | − |
| H146 | + |
| H196 | − |

D) Netrin-1 expression in other human tumors.

Expression of netrin-1 examined by Q-RT PCR using total RNA extracted from different human tumors as in FIGS. 10A-10B, 11A-11C, 12A-12B. The table 10 indicates (n) the number of tumors tested and the percentage of tumors showing an overexpression of netrin-1 in each pathology;

TABLE 10

| Cancers | n | over expression of netrin-1 |
|---|---|---|
| Renal adenocarcinoma | 5 | 40% |
| Acute myeloid leukaemia | 55 | 62% |
| Sarcoma | 10 | 30% |
| Melanoma | 6 | 50% |
| Ovarian adenocarcinoma | 14 | 93%* |
| Pancreatic adenocarcinoma | 7 | 57% |
| Uterus adenocarcinoma | 42 | 19% |
| Stomac adenocarcinoma | 27 | 26% |
| Kidney adenocarcinoma | 20 | 50% |
| Rectal adenocarcinoma | 18 | 17% |

*100% of the 7 metastatic samples

EXAMPLE 5

To analyze whether DCC was under its monomeric form unless netrin-1 was present, we transiently co-expressed an HA-tagged full-length DCC together with c-myc-tagged full-length DCC in HEK293T cells. Immunoprecipitation was then performed using an anti-c-myc antibody and as shown in FIG. 12A, despite a good expression of both HA and c-myc tagged-DCC, HA-DCC was only modestly included in the c-myc-DCC pull-down in absence of ligand, suggesting that DCC, was mainly present as a monomer when expressed in HEK293T in the absence of netrin-1. In the same experimental conditions, when netrin-1 was added to the culture medium (not shown and FIG. 15C) or when a netrin-1 expression construct was co-expressed with the DCC-expressing constructs (FIG. 11A), HA-DCC was clearly included in the c-myc DCC pull-down, hence demonstrating that netrin-1 triggers dimerisation or multimerization of DCC. This result is in agreement with data from Tessier-Lavigne and colleagues who first reported netrin-1-induced multimerization[46], even though in our culture and immunoprecipitation conditions, DCC displays a modest albeit detectable level of multimerization in the absence of netrin-1. This constitutive, low multimerization level could either be attributed to the low affinity of DCC receptors for themselves in the absence of ligand or to the system used, which is base don forced expression of high levels of transmembrane receptors.

We then investigated whether the other UNC5H netrin-1 receptors share a similar behaviour. HEK293T cells were transiently transfected with an HA-tagged full-length UNC5H2 together with Flag-tagged full-length UNC5H2 in the presence or absence of netrin-1, Immunoprecipitation was the performed using an anti-FlagM2 antibody. As shown in FIG. 11B, the presence of netrin-1 triggers an efficient immunoprecipitation of HA-UNC5H2 with Flag-UNC5H2. Thus, while in the absence of netrin-1, DDC and UNC5H2 are mainly under monomeric forms, both DCC and UNC5H2 show an increased propensity to multimerize in the presence of netrin-1.

To determine whether netrin-1-induced multimerization is the crucial step for inhibiting DCC/UNC5H2 pro-apoptotic cell death, we developed a chimeric system in which protein dimerization can be induced by a chemical agent. This system was successfully used to show both the role of caspase-8 dimerization in caspase-8 activation[49] and the importance of p75ntr-multimerization in p75ntr pro-apoptotic activity[48]. This system is derived from the ability of the Fk1012 compound to cross-dimerize the FkBP motif. DCC and UNC5H2 intracellular domains were fused in their N-terminus to derived Fv2e FkBP motives and dimerization was induced using the AP20187 chemical compound (FIG. 13A). We first analyzed whether the developed system recapitulates netrin-1-induced multimerization of the UNC5H2 intracellular domain. HEK293T cells were co-transfected with an HA-tagged Fv2e-UNC5H2-IC together with c-myc-tagged Fv2e-UNC5H2-IC and co-immunoprecipitations were performed using an anti-c-myc antibody. As shown in FIG. 13B, without addition of AP20187, HA-Fv2e-UNC5H2-IC was barely detectable in the c-myc-Fv2e-UNC5H2-IC pull-down, hence supporting that Fv2e-UNC5H2-IC is expressed in HEK293T cells mainly as a monomer. As expected, addition of AP20187 led to the efficient pull-down of HA-Fv2e-UNC5H2-IC with c-myc-Fv2e-UNC5H2-IC. Similar results were obtained with Fv2e-DCC-IC (not shown). Thus, this dimerization system recapitulates dimerization of the intracellular domain of the netrin-1 receptors DCC and UNC5H2.

Because this chemically-inducible DCC/UNC5H2 dimerization system appears to work adequately to mimic netrin-1 induced DCC/UNC5H2 multimerization, we then assessed whether the dimerization of DCC/UNC5H2 was sufficient to inhibit DCC/UNC5H2 pro-apoptotic activity. HEK293T cells were forced to express Fv2e-DCC-IC in the presence or absence of AP20187 and cell death was assessed by trypan blue staining, as previously described, to measure DCC-induced cell death[6, 27]. As shown in FIG. 14A, expression of Fv2e-DCC-IC was associated with increased cell death compared to expression of the Fv2e motives without the DCC-IC fusion. Interestingly, when AP20187 was added, cell death induced by Fv2e-DCC-IC was dramatically reduced (FIG. 14A). Similarly, while Fv2e-UNC5H2-IC triggers cell death (FIG. 14B) or caspase activation (FIG. 14C) when expressed in HEK293T in the absence of AP20187, the addition of the dimerizing drug is sufficient to reduce significantly Fv2e-UNC5H2-IC-induced cell death (FIG. 14B) or caspase activation (FIG. 14C). Thus, while monomeric DCC-IC and UNC5H2-IC are pro-apoptotic, the multimeric forms of DCC-IC or UNC5H2-IC no longer display pro-apoptotic activity. Therefore, the ability of netrin-1 to inhibit DCC/UNC5H2-pro-apoptotic activity is intrinsically linked to the ability of netrin-1 to multimerize DCC or UNC5H2, as this multimerization process is sufficient to shut down DCC and UNC5H2 pro-apoptotic activity.

A tempting model would be that the monomeric form of DCC or UNC5H2 has a spatial conformation that is easily subjected to the initial caspase cleavage of the receptor's intracellular domain. On the opposite, presence of the ligand would lead to multimerization of the intracellular domain, which somehow becomes less accessible to caspase cleavage. Along this line, Arakawa and colleagues have shown that the caspase cleavage of UNC5H2 is inhibited by netrin-1 presence[47]. Yet, because of technical limitations, we have failed to detect DDC or UNC5H2 cleavage in cells forced to express the Fv2e fusion proteins. An alternative model to the cleavage inhibition would be that netrin-1-induced receptor multimerization triggers a survival signal, that somehow inhibits a constitutive pro-apoptotic activity of DCC or UNC5H2 related to constitutive caspase cleavage. However, we failed to show that the known positive signalling pathways activated by DCC upon netrin-1 binding are involved in the inhibitory activity of netrin-1 on DCC pro-apoptotic activity. For example, netrin-1 induces DCC-mediated activation of ERK-1/2[3], kinases known to display an anti-apoptotic effect. However, classic inhibitors of the ERK-1/2 pathway, while affecting netrin-1-induced ERK-1/2 phosphorylation, failed to block the netrin-1-inhibitory effect on DDC pro-apoptotic activity (Forcet and Mehlen, unpublished). Thus, it is probable that netrin-1-induced DCC multimerization affects DCC intracellular accessibility. However, it remains to be demonstrated whether this is a matter of simple stochiometry, or whether the brining closer of the extracellular domains induces a change of conformation within the intracellular compartments.

If the mechanisms underlying netrin-1-induced receptor multimerization are yet to be described, the observation that netrin-1-induced DCC/UNC5H2 multimerization is sufficient to inhibit DC/UNC5H2-induced cell death may represent an interesting tool to turn on DCC or UNC5H pro-apoptotic activity in vivo, in tumors in which netrin-1 is expressed in an autocrine manner. Indeed, we have demonstrated that netrin-1 overexpression in mice gut is associated with intestinal tumor development because of apoptosis inhibition[18] and we have recently observed that netrin-1 is overexpressed in the majority of human metastastic breast cancers. Moreover, the mechanism of netrin-1 overexpression appears to be an acquired selective advantage of metastatic tumor cells for survival in settings of environmental absence of netrin-1 (see examples 2 and 3). Thus, to inhibit DCC/UNC5H dimerization would putatively represent an interesting way to trigger tumor cell apoptosis.

Along this line, the fifth fibronectin domain of DCC has been shown to be a domain of interaction with netrin-1 (FIG. 15A and [21]), even though conflicting data have also been reported[43]. We thus first assessed whether a recombinant soluble fifth fibronectin domain of DCC (DCC-5Fbn) could bind to recombinant netrin-1. ELISA assay demonstrates that DCC-5Fbn specifically binds to netrin-1, as opposed to the extracellular domain of an unrelated receptor, IL3-R (FIG. 15A). The approximate Kd for DCC-5Fbn/netrin-1 was roughly estimated at 5 nM, in keeping with the order of magnitude of the described DCC/netrin-1 Kd. We next investigated whether this domain was sufficient to displace DCC/netrin-1 interaction. As shown in FIG. 15B, using an ELISA assay in which the extracellular domain of DCC was coated and netrin-1/DCC interaction was detected by netrin-1 immunoreactivity, we observed that, while as a positive control the complete extracellular domain of DCC (DCC-EC) was sufficient to displace DCC/netrin-1 interaction, DCC-5Fbn failed to interfere. Thus, DCC-5Fbn interacts with netrin-1 but is not sufficient to inhibit DCC/netrin-1 interaction. We next investigated whether DCC-5Fbn could influence DCC multimerization. We performed co-immunoprecipitation in HEK293T transiently transfected with HA-tagged full-length DCC together with c-myc-DCC, full-length DCC in the presence or absence of netrin-1. As also described in FIG. 1A, presence of netrin-1 triggers the immunoprecipitation of HA-DCC with c-myc-DCC, demonstrating netrin-1-induced DCC multimerization (FIG. 15C). However, when the cells incubated with netrin-1 were also simultaneously treated with DCC-5Fbn, the HA-DCC/c-myc-DCC interaction returns to netrin-1 non-treated levels. Thus, DCC-5Fbn interacts with netrin-1 in a region responsible for the netrin-1-mediated coming closer of two or more DCC molecules and is able to inhibit netrin-1-induced DCC-multimerization.

We then tested whether DCC-5Fbn could consequently trigger netrin-1 receptors-induced cell death. To this purpose, HEK293T cells were forced to express DCC in the presence or absence of netrin-1, with or without DCC-5Fbn, and cell death was determined by trypan blue exclusion assay (FIG. 16A). As shown in FIG. 16A, while DCC triggers apoptosis in the absence of netrin-1, a pro-apoptotic activity blocked by the presence of netrin-1, the presence of DCC-5Fbn is sufficient to block the inhibitory activity of netrin-1, thus leading to DCC-induced cell death. Because the HEK293T cell system uses ectopic expression of netrin-1, we next rested DCC-5Fbn in a more biologically relevant model. We recently demonstrated that compared to non-metastatic breast cancers, the majority of human metastatic breast cancers overexpresses netrin-1. We have also shown that titrating overexpressed netrin-1 triggers tumor cell apoptosis in vitro and metastasis inhibition in mice (see Examples 2 and 3). Many breast tumor cell lines appear to express netrin-1 and we have shown that titrating netrin-1 in mice breast carcinoma 4T1 cells triggers apoptosis (see Examples 2 and 3). As shown in FIG. 16B, addition of DCC-5Fbn to a 4T1 cell culture is associated with increased cell death.

Taken together, we have shown here that the multimerization of the dependence receptors DCC and UNC5H is a sufficient mechanism to block their pro-apoptotic activity. Interestingly, this inhibitory mechanism appears to mirror what is observed with death receptors. Indeed, it is known that TNRr or Fas requires trimerization to induce apoptosis[45]. This intrinsic difference may therefor represent an added-value for therapeutic strategies using dependence receptors. Indeed, the search of therapeutic molecules in the past has mainly led to hits that act on the inhibition of cellular processes—e.g., kinases inhibitors, IAP inhibitors—rather than activators. As a consequence, inhibition of netrin-1 receptors multimerization via the use of recombinant DCC-5Fbn or via any compound screened to interfere with receptor multimerization appears as a tempting strategy for the treatment of cancers in which netrin-1 autocrine expression has been acquired.

Here, we show that netrin-1 triggers the multimerization of both DCC and UNC5H receptors. By using a system in which dimerization is chemically-induced, we demonstrate that multimerization of the intracellular domain of netrin-1 receptors, such as DCC and UNC5H2, is the critical step to inhibit their pro-apoptotic activity. We therefore propose a model in which monomeric netrin-1-dependence receptors are pro-apoptotic, while their multimerization, induced by netrin-1, abolishes their pro-apoptotic activity. Using this property, we propose the use of a recombinant specific domain of the DCC extracellular region that (i) interacts with netrin-1 and (ii) inhibits netrin-1-induced multimerization, in order to trigger apoptosis of tumor cells.

REFERENCES

1. Serafini, T. et al. Netrin-1 is required for commissural axon guidance in the developing vertebrate nervous system. *Cell* 87, 1001-14 (1996).
2. Keino-Masu, K. et al. Deleted in Colorectal Cancer (DCC) encodes a netrin receptor, *Cell* 87, 175-85 (1996).
3. Forcet. C. et al. Netrin-1-mediated axon outgrowth required deleted in colorectal cancer-dependent MAPK activation, *Nature* 417, 443-7 (2002).
4. Ackerman, S. L. et al. The mouse rostral cerebellar malformation gene encodes an UNC-5-like protein, *Nature* 386, 838-42 (1997).
5. Hong, K. et al. A ligand-gated association between cytoplasmic domains of UNC5 and DCC family receptors convers netrin-induced growth cone attraction to repulsion. *Cell* 97, 927-41 (1999).
6. Mehlen P. et al. The DCC gene product induces apoptosis by a mechanism requiring receptor proteolysis. *Nature* 395, 801-4 (1998).
7. Llambi, F., Causeret, F., Bloch-Gallego, E. & Mehlen, P. Netrin-1 acts as a survival factor via its receptors UNC5H and DCC. *Embo J* 20, 2715-22 (2002).
8. Bordeaux, M. C. et al. The RET proto-oncogene induces apoptosis: a novel mechanism for Hirschsprung disease. *Embo J* 19, 4056-63 (2000).
9. Stupack, D. G., Puente, X. S., Boutsaboualoy, S., Storgard, C. M. & Cheresh, D. A. Apoptosis of adherent cells by recruitment of caspase-8 to unligated integrins. *J Cell Biol* 155, 459-70 (2001).
10. Thibert, C. et. al. Inhibition of neuroepithelial patched-induced apoptosis by sonic hedgehog. *Science* 301, 843-6 (2003).
11. Matsunaga, E. et al. RGM and its receptor neogenin regulate neuronal survival. *Nat Cell Biol* 6, 749-55 (2004).
12. Rabizadeh, S. et al. Induction of apoptosis by the low-affinity NGF receptor. *Science* 261, 345-8 (1993).
13. Mehlen, P. & Thibert, C. Dependence receptors: between life and death. *Cell Mol. Life Sci* 61, 1854-66 (2004).
14. Bredesen, D. E., Mehlen, P. & Rabizadeh, S. Receptors that mediate cellular dependence. *Cell Death Differ* 12, 1031-43 (2005).
15. Fearon, E. R. et al. Identification of a chromosome 18q gene that is altered in colorectal cancers. *Science* 247, 49-56 (1990).
16. Kinzler, K. W. & Vogelstein, B. Lessons from hereditary colorectal cancer. *Cell* 87, 159-70 (1996).
17. Thiebault, K. et al. The netrin-1 receptors UNC5H are putative tumor suppressors controlling cell death commitment. *Proc Natl Acad Sci USA* 100, 4173-4178 (2003).
18. Mazelin, L. et al. Netrin-1 controls colorectal tumorigenesis by regulating apoptosis. *Nature* 431, 80-4 (2004).
19. Bernet, A. et al. The netrin-1 receptor UNC5H3 is a tumor suppressor in colorectal malignancies, submitted (2007).
20. Aslakson, C. J. & Miller, F. R. Selective events in the metastatic process defined by analysis of the sequential dissemination of subpopulations of a mouse mammary tumor. *Cancer Res* 52, 1399-405 (1992).
21. Geisbrecht, B. V., Dowd, K. A. Barfield, R. W., Longo, P. A. & Leahy, D. J. Netrin binds discrete subdomains of DCC and UNC5 and mediates interactions between DCC and heparin. *J. Biol Chem* 278, 32561-8 (2003).
22. Llambi, F. et al. The dependence receptor UNC5H2 mediates apoptosis through DAP-kinase. *Embo J* 24, 1192-201 (2005).
23. Inbal, B. et al. DAP kinase links the control of apoptosis to metastasis. *Nature* 390, 180-4 (1997).
24. Andre, F. et al. Breast cancer with synchronous metastases; trends in survival during a 14-year period. *J. Clin Oncol* 22, 3302-8 (2004).
25. de Cremoux, P. et al. Inter-laboratory quality control for hormone-dependent gene expression in human breast tumors using real-time reverse transcription-polymerase chain reaction. *Endocr Relat Cancer* 11, 489-95 (2004).
26. Latil, A. et al. Quantification of expression of netrins, slits and their receptors in human prostate tumors. *Int J Cancer* 103, 305-15 (2003).
27. Forcet, C., Ye, X., Granger L., Corset, V., Shin, H., Bredesen, D. E. and Mehlen, P. (2001) The dependence receptor DCC (deleted in colorectal cancer) defines an alternative mechanism for caspase activation. Proc Natl Acad Sci USA, 98, 3416-3421.
28. de Kok, J. B. et al. Normalization of gene expression measurements in tumor tissues: comparison of 13 endogenous control genes. Lab Invest 85, 154-9 (2005).
29. Mehlen, P. & Fearon, E. R. Role of the dependence receptor DCC in colorectal cancer pathogenesis. J Clin Oncol 22, 3420-8 (2004).
30. Stupack, D. G. et al. Potentiation of neuroblastoma metastasis by loss of caspase-8. Nature 439, 95-9 (2006).
31. Serafini, T. et al. The netrins define a family of axon outgrowth-promoting proteins homologous to *C. elegans* UNC-6. Cell 78, 409-24 (1994).
32. Yebra, M. et al. Recognition of the neural chemoattractant Netrin-1 by integrins alpha6beta4 and alpha3beta1 regulates epithelial cell adhesion and migration. Dev Cell 5, 695-707 (2003).
33. Srinivasan, K., Strickland, P., Valdes, A., Shin, G. C. & Hinck, L. Netrin-1/neogenin interaction stabilizes multipotent progenitor cap cells during mammary glad morphogenesis. Dev Cell 4, 371-82 (2003).
34. Liu, Y. et al. Novel role for Netrins in regulating epithelial behavior during lung branching morphogenesis. Curr Biol 14, 897-905 (2004).
35. Park, K. W. et al. The axonal attractant Netrin-1 is an angiogenic factor. Proc Natl Acad Sci USA 101, 16210-5 (2004).
36. Lu, X. et al. The netrin receptor UNC5B mediates guidance events controlling morphogenesis of the vascular system. Nature 432, 179-86 (2004).
37. Nguyen, A. & Cai, H. Netrin-1 induces angiogensis via a DCC-dependent ERK1/2-eNOS feed-forward mechanism. Proc Natl Acad Sci USA 103, 6530-5 (2006).
38. Wilson, B. D. et al. Netrins Promote Developmental and Therapeutic Angiogenesis, Science (2006).
39. Chan, S. D., Zheng, H., Su, M. W., Wilk, R., Killeen, M. T., Hedgecock, E. M. and Culotti, J. G. (1996) UNC-40, a *C. elegans* homolog of DCC (Deleted in Colorectal Cancer) is required in motile cells responding to UNC-6 netrin cues. Cell, 87, 187-195.
40. Ellerby, L. M., Hackam, A. S., Propp, S. S., Ellerby, H. M., Rabizadeh, S., Cashman, N. R., Trifiro, M. A., Pinsky, L., Wellington, C. L., Salvesen, G. S., Hayden, M. R. and Bredesen, D. E. (1999) Kennedy's disease: caspase cleavage of the androgen receptor is a crucial event in cytotoxicity. J Neurochem, 72, 185-195.
41. Fazeli, A., Dickinson, S. L., Hermiston, M. L., Tighe, R. V., Steen, R. G., Small, C. G., Stoeckli, E. T., Keino-Masu, K. Masu, M., Rayburn, H., Simons, J., Bronson, R.

T., Gordon, J. I., Tessier-Lavigne, M. and Weinberg, R. A. (1997) Phenotype of mice lacking functional Deleted in colorectal cancer (Dcc) gene. Nature, 386, 796-804.
42. Hedgecock, E. M. Culotti, J. G. and Hall, D. H. (1990) The unc-5, unc-6, and unc-40 genes guide circumferential migrations of pioneer axons and mesodermal cells on the epidermis in *C. elegans*. Neuron, 4, 61-85.
43. Kruger, R. P., Lee J., Li, W. and Guan, K. L. (2004) Mapping netrin receptor binding reveals domains of Unc5 regulating its tyrosine phosphorylation. J. Neurosci, 24, 10826-10834.
44. Mehlen, P. and Bredesen, D. E. (2004) The dependence receptor hypothesis. Apoptosis, 9, 37-49.
45. Muppidi, J. R., Tschopp, J. and Siegel, R. M. (2004) Life and death decisions: secondary complexes and lipid rafts in TNF receptor family signal transduction. Immunity, 21, 461-465.
46. Stein, E., Zou, Y., Poo, M. and Tessier-Lavigne, M. (2001) Binding of DCC by netrin-1 to mediate axon guidance independent of adenosine A2B receptor activation. Science, 291, 19761982.
47. Tanikawa, C., Matsuda, K., Fukuda, S., Nakamura, Y. and Arakawa, H. (2003) p 53RDL1 regulates p53-dependent apoptosis. Nat Cell Biol, 5, 216-223.
48. Wang, J. J., Rabizadeh, S., Tasinato, A., Sperandio, S., Ye, X., Green, M., Assa-Munt, N., Spencer, D. and Bredesen, D. E. (2000) Dimerization-dependent block of the proapoptotic effect of p75(NTR, J Neurosci Res, 60, 587-593.
49. Yang, X., Chang, H. Y. and Baltimore, D. (1998) Autoproteolytic activation of pro-caspases by oligomerization. Mol Cell, 1, 319-325.
50. Mehlen P. and C. Furne (2005) Netrin-1: when a neuronal guidance cue turns out to be a regulator of tumorigenesis. Cell Mol Life Sci. 62:2599-616.

The invention claimed is:

1. A method for detecting a high level of netrin-1 in a tumor of a human patient and treating said human patient, said tumor being selected from the group consisting of breast cancer, lung cancer, neuroblastoma, glioma, leukemia, sarcoma, melanoma and adenocarcinoma, said method comprising the steps of:
  (a) obtaining a tumor biopsy sample from said patient and quantifying a netrin-1 expression product level in said tumor biopsy sample, wherein said product is (i) RNA encoding netrin-1 or (ii) netrin-1 protein; and
  (b) comparing said netrin-1 expression product level quantified at step (a) with netrin-1 expression product level quantified in a non-metastatic tumor biopsy, and calculating a ratio between netrin-1 expression product level quantified in step (a) in the biopsy sample and netrin-1 expression product level quantified in the non-metastatic reference biopsy;
  (c) detecting whether a calculated ratio above 3 exists between netrin-1 expression product level quantified in step (a) in the tumor biopsy sample and netrin-1 expression product level in the non-metastatic reference biopsy; and
  (d) if the calculated ratio is above 3, whereby the human patient is indicated to have a metastatic cancer, administering to the human patient an effective amount of (1) a monoclonal antibody or (2) a compound comprising an extracellular domain of netrin-1 receptor or fragment thereof, to:
    (i) inhibit interaction between netrin-1 and said netrin-1 receptor in the tumor, or
    (ii) inhibit dimerization or multimerization of an intracellular domain of said netrin-1 receptor in the tumor.

2. The method of claim 1, wherein the biopsy sample is from a patient being treated with an anti-cancer treatment.

3. The method according to claim 1, wherein the measuring step comprises measuring said RNA encoding netrin-1 by a quantitative real time reverse polymerase chain reaction (PCR) method.

4. The method according to claim 1, wherein the measuring step comprises measuring said netrin-1 protein using specific antibodies able to specifically recognize said netrin-1 protein.

5. The method according to claim 1, wherein the tumor is selected from the group consisting of breast cancer, lung cancer, neuroblastoma, and glioma.

6. The method according to claim 1, wherein said tumor is selected from the group consisting of ovarian adenocarcinoma, renal adenocarcinoma, pancreatic adenocarcinoma, uterus adenocarcinoma, stomach adenocarcinoma, kidney adenocarcinoma and rectal adenocarcinoma.

7. The method of claim 1, wherein the calculated ratio is above 3, the patient is treated with an effective amount of a monoclonal antibody, and said breast cancer, lung cancer, neuroblastoma, glioma, leukemia, sarcoma, melanoma and adenocarcinoma are metastatic.

8. The method of claim 1, wherein the patient is treated with an effective amount of a compound comprising an extracellular domain of netrin-1 receptor or fragment thereof.

9. The method of claim 8, wherein said extracellular domain of netrin-1 receptor or fragment thereof is selected from the group consisting of DCC, UNC5H, neogenin, and adenosine A2b.

10. The method of claim 8, wherein said compound comprises an extracellular domain of DCC.

11. The method of claim 8, wherein said compound is DCC-EC-Fc or DCC-5Fbn.

12. The method of claim 8, wherein said tumor is selected from the group consisting of ovarian adenocarcinoma, renal adenocarcinoma, pancreatic adenocarcinoma, uterus adenocarcinoma, stomach adenocarcinoma, kidney adenocarcinoma and rectal adenocarcinoma.

13. The method of claim 8, wherein said breast cancer, lung cancer, neuroblastoma, glioma, leukemia, sarcoma, melanoma and adenocarcinoma are metastatic.

* * * * *

SEQUENCE LISTING

```
<160> NUMBER OF SEQ ID NOS: 29

<210> SEQ ID NO 1
<211> LENGTH: 62
<212> TYPE: DNA
<213> ORGANISM: Artificial sequence
<220> FEATURE:
<223> OTHER INFORMATION: Primer used for introducing a HA tag in the
      template pCMV-DCC

<400> SEQUENCE: 1
cacaggctca gcctttatc catatgatgt accggattat gcataacatg tatttctgaa     60
tg                                                                   62

<210> SEQ ID NO 2
<211> LENGTH: 62
<212> TYPE: DNA
<213> ORGANISM: Artificial sequence
<220> FEATURE:
<223> OTHER INFORMATION: Primer used for introducing a HA tag in the
      template pCMV-DCC

<400> SEQUENCE: 2
cattcagaaa tacatgttat gcataatccg gtacatcata tggataaaag gctgagcctg     60
tg                                                                   62

<210> SEQ ID NO 3
<211> LENGTH: 65
<212> TYPE: DNA
<213> ORGANISM: Artificial sequence
<220> FEATURE:
<223> OTHER INFORMATION: Primer used for introducing a c-myc tag in the
      template pCMV-DCC

<400> SEQUENCE: 3
cacaggctca gcctttgagc agaagttgat aagtgaggaa gatctgtaac atgtatttct     60
gaatg                                                                65

<210> SEQ ID NO 4
<211> LENGTH: 65
<212> TYPE: DNA
<213> ORGANISM: Artificial sequence
<220> FEATURE:
<223> OTHER INFORMATION: Primer used for introducing a c-myc tag  in the
      template pCMV-DCC
```

```
<400> SEQUENCE: 4
cattcagaaa tacatgttac agatcttcct cacttctcaa cttctgctca aaggctgagc      60
ctgtg                                                                  65

<210> SEQ ID NO 5
<211> LENGTH: 33
<212> TYPE: DNA
<213> ORGANISM: Artificial sequence
<220> FEATURE:
<223> OTHER INFORMATION: Primer used for obtaining a PCR fragment of the
      intracellular domain of DCC (1122-1447)

<400> SEQUENCE: 5
tatgtcgacc gacgctcttc agcccagcag aga                                   33

<210> SEQ ID NO 6
<211> LENGTH: 72
<212> TYPE: DNA
<213> ORGANISM: Artificial sequence
<220> FEATURE:
<223> OTHER INFORMATION: Primer used for obtaining a PCR fragment of the
      intracellular domain of DCC (1122-1447)

<400> SEQUENCE: 6
tatgaattct tagtcgagtg cgtagtctgg tacgtcgtac ggataaaagg ctgagcctgt      60
gatggcatta ag                                                          72

<210> SEQ ID NO 7
<211> LENGTH: 78
<212> TYPE: DNA
<213> ORGANISM: Artificial sequence
<220> FEATURE:
<223> OTHER INFORMATION: Primer used for obtaining c-myc-Fv2E-DCC-IC

<400> SEQUENCE: 7
cttaatgcca tcacaggctc agcctttgaa cagaaactca tctctgaaga ggatctgtaa      60
gaattcataa agggcaat                                                    78

<210> SEQ ID NO 8
<211> LENGTH: 78
<212> TYPE: DNA
<213> ORGANISM: Artificial sequence
<220> FEATURE:
<223> OTHER INFORMATION: Primer used for obtaining c-myc-Fv2E-DCC-IC

<400> SEQUENCE: 8
attgcccttt atgaattctt acagatcctc ttcagagatg agtttctgtt caaaggctga      60
gcctgtgatg gcattaag                                                    78

<210> SEQ ID NO 9
<211> LENGTH: 25
<212> TYPE: DNA
<213> ORGANISM: Artificial sequence
<220> FEATURE:
<223> OTHER INFORMATION: Primer used for the constructs encoding FlagM2-
      UNC5H2

<400> SEQUENCE: 9
gcgcggccgc agggcccgga gcggg                                            25

<210> SEQ ID NO 10
<211> LENGTH: 30
<212> TYPE: DNA
```

<213> ORGANISM: Artificial sequence
<220> FEATURE:
<223> OTHER INFORMATION: Primer used for the constructs encoding FlagM2-
      UNC5H2

<400> SEQUENCE: 10
cggaattctc agcaatcgcc atcagtggtc                                    30

<210> SEQ ID NO 11
<211> LENGTH: 26
<212> TYPE: DNA
<213> ORGANISM: Artificial sequence
<220> FEATURE:
<223> OTHER INFORMATION: Primer used for generating by PCR amplification
      of the UNC5H2-HA intracellular domain

<400> SEQUENCE: 11
cggtcgacgt gtaccggaga aactgc                                        26

<210> SEQ ID NO 12
<211> LENGTH: 57
<212> TYPE: DNA
<213> ORGANISM: Artificial sequence
<220> FEATURE:
<223> OTHER INFORMATION: Primer used for generating by PCR amplification
      of the UNC5H2-HA intracellular domain

<400> SEQUENCE: 12
gcgaattctc atgcataatc cggcacatca tacggatagc aatcgccatc agtggtc      57

<210> SEQ ID NO 13
<211> LENGTH: 26
<212> TYPE: DNA
<213> ORGANISM: Artificial sequence
<220> FEATURE:
<223> OTHER INFORMATION: Primer used for generating by PCR amplification
      of the UNC5H2-myc intracellular domain

<400> SEQUENCE: 13
cggtcgacgt gtaccggaga aactgc                                        26

<210> SEQ ID NO 14
<211> LENGTH: 60
<212> TYPE: DNA
<213> ORGANISM: Artificial sequence
<220> FEATURE:
<223> OTHER INFORMATION: Primer used for generating by PCR amplification
      of the UNC5H2-myc intracellular domain

<400> SEQUENCE: 14
gcgaattctc acagatcctc ttctgagatg agtttttgtt cgcaatcgcc atcagtggtc   60

<210> SEQ ID NO 15
<211> LENGTH: 18
<212> TYPE: DNA
<213> ORGANISM: Artificial sequence
<220> FEATURE:
<223> OTHER INFORMATION: Fv2E forward primer

<400> SEQUENCE: 15
ccaccatggg gagtagca                                                 18

<210> SEQ ID NO 16
<211> LENGTH: 49
<212> TYPE: DNA
<213> ORGANISM: Artificial sequence
<220> FEATURE:

```
<223> OTHER INFORMATION: UNC5H2-HA reverse primer

<400> SEQUENCE: 16
tcatgcataa tccggcacat catacggata gcaatcgcca tcagtggtc                49

<210> SEQ ID NO 17
<211> LENGTH: 52
<212> TYPE: DNA
<213> ORGANISM: Artificial sequence
<220> FEATURE:
<223> OTHER INFORMATION: UNC5H2-myc reverse primer

<400> SEQUENCE: 17
tcacagatcc tcttctgaga tgagtttttg ttcgcaatcg ccatcagtgg tc            52

<210> SEQ ID NO 18
<211> LENGTH: 23
<212> TYPE: DNA
<213> ORGANISM: Artificial sequence
<220> FEATURE:
<223> OTHER INFORMATION: Primer used for expressed human PBGD as
      internal control

<400> SEQUENCE: 18
ctggagttca ggagtattcg ggg                                            23

<210> SEQ ID NO 19
<211> LENGTH: 24
<212> TYPE: DNA
<213> ORGANISM: Artificial sequence
<220> FEATURE:
<223> OTHER INFORMATION: Primer used for expressed human PBGD as
      internal control

<400> SEQUENCE: 19
cagatccaag atgtcctggt cctt                                           24

<210> SEQ ID NO 20
<211> LENGTH: 20
<212> TYPE: DNA
<213> ORGANISM: Artificial sequence
<220> FEATURE:
<223> OTHER INFORMATION: Primer used for expressed human TBP as internal
      control

<400> SEQUENCE: 20
cacgaaccac ggcactgatt                                                20

<210> SEQ ID NO 21
<211> LENGTH: 22
<212> TYPE: DNA
<213> ORGANISM: Artificial sequence
<220> FEATURE:
<223> OTHER INFORMATION: Primer used for expressed human TBP as internal
      control

<400> SEQUENCE: 21
ttttcttgct gccagtctgg ac                                             22

<210> SEQ ID NO 22
<211> LENGTH: 21
<212> TYPE: DNA
<213> ORGANISM: Artificial sequence
<220> FEATURE:
<223> OTHER INFORMATION: Primer used for expressed human netrin-1-NTN1
      as internal control
```

<400> SEQUENCE: 22
tgcaagaagg actatgccgt c                                              21

<210> SEQ ID NO 23
<211> LENGTH: 21
<212> TYPE: DNA
<213> ORGANISM: Artificial sequence
<220> FEATURE:
<223> OTHER INFORMATION: Primer used for expressed human human netrin-1-
      NTN1 as internal control

<400> SEQUENCE: 23
gctcgtgccc tgcttataca c                                              21

<210> SEQ ID NO 24
<211> LENGTH: 20
<212> TYPE: DNA
<213> ORGANISM: Artificial sequence
<220> FEATURE:
<223> OTHER INFORMATION: Primer used for expressed human UNC5B as
      internal control

<400> SEQUENCE: 24
tgcaggagaa cctcatggtc                                                20

<210> SEQ ID NO 25
<211> LENGTH: 20
<212> TYPE: DNA
<213> ORGANISM: Artificial sequence
<220> FEATURE:
<223> OTHER INFORMATION: Primer used for expressed human UNC5B as
      internal control

<400> SEQUENCE: 25
gggctggagg attactggtg                                                20

<210> SEQ ID NO 26
<211> LENGTH: 25
<212> TYPE: DNA
<213> ORGANISM: Artificial sequence
<220> FEATURE:
<223> OTHER INFORMATION: Primer used for expressed human DCC as internal
      control

<400> SEQUENCE: 26
agccaatggg aaaattactg cttac                                          25

<210> SEQ ID NO 27
<211> LENGTH: 25
<212> TYPE: DNA
<213> ORGANISM: Artificial sequence
<220> FEATURE:
<223> OTHER INFORMATION: Primer used for expressed human DCC as internal
      control

<400> SEQUENCE: 27
aggttgagat ccatgatttg atgag                                          25

<210> SEQ ID NO 28
<211> LENGTH: 26
<212> TYPE: DNA
<213> ORGANISM: Artificial sequence
<220> FEATURE:
<223> OTHER INFORMATION: Primer used for expressed human UNC5C as
      internal control

<400> SEQUENCE: 28
gcaaattgct ggctaaatat caggaa                                          26

<210> SEQ ID NO 29
<211> LENGTH: 26
<212> TYPE: DNA
<213> ORGANISM: Artificial sequence
<220> FEATURE:
<223> OTHER INFORMATION: Primer used for expressed human UNC5C as
      internal control

<400> SEQUENCE: 29
gctccactgt gttcaggcta aatctt                                          26